US008124582B2

(12) United States Patent
Guenzler-Pukall et al.

(10) Patent No.: US 8,124,582 B2
(45) Date of Patent: Feb. 28, 2012

(54) TREATMENT OF DIABETES

(75) Inventors: Volkmar Guenzler-Pukall, San Leandro, CA (US); Stephen J. Klaus, San Francisco, CA (US); Ingrid Langsetmo Parobok, Milpitas, CA (US); Todd W. Seeley, Moraga, CA (US)

(73) Assignee: FibroGen, Inc., San Francisco, CA (US)

( * ) Notice: Subject to any disclaimer, the term of this patent is extended or adjusted under 35 U.S.C. 154(b) by 632 days.

(21) Appl. No.: 10/729,704

(22) Filed: Dec. 4, 2003

(65) Prior Publication Data
US 2004/0204356 A1 Oct. 14, 2004

Related U.S. Application Data

(60) Provisional application No. 60/431,351, filed on Dec. 6, 2002, provisional application No. 60/476,331, filed on Jun. 6, 2003, provisional application No. 60/476,726, filed on Jun. 6, 2003.

(51) Int. Cl.
*A61K 38/17* (2006.01)
(52) U.S. Cl. ............................. 514/3; 514/1.9; 514/15.4
(58) Field of Classification Search .................. None
See application file for complete search history.

(56) References Cited

U.S. PATENT DOCUMENTS

| 5,607,954 | A | 3/1997 | Weidmann et al. |
| 5,610,172 | A | 3/1997 | Weidmann et al. |
| 5,620,995 | A | 4/1997 | Weidmann et al. |
| 5,620,996 | A | 4/1997 | Weidmann et al. |
| 5,658,933 | A | 8/1997 | Weidmann et al. |
| 5,719,164 | A | 2/1998 | Weidmann et al. |
| 5,726,305 | A | 3/1998 | Weidmann et al. |
| 5,916,898 | A * | 6/1999 | Edwards et al. ............... 514/292 |
| 5,942,434 | A | 8/1999 | Ratcliffe et al. |
| 6,020,350 | A | 2/2000 | Weidmann et al. |
| 6,093,730 | A | 7/2000 | Weidmann et al. |
| 6,124,131 | A | 9/2000 | Semenza |
| 6,159,996 | A | 12/2000 | Jaehne et al. |
| 6,200,974 | B1 | 3/2001 | Edwards et al. |
| 6,562,799 | B1 | 5/2003 | Semenza |
| 7,618,940 | B2 * | 11/2009 | Fourney et al. ............... 514/1.1 |
| 2004/0235082 | A1 | 11/2004 | Fourney et al. |
| 2006/0178316 | A1 | 8/2006 | Klaus et al. |
| 2006/0178317 | A1 | 8/2006 | Klaus et al. |
| 2006/0183695 | A1 | 8/2006 | Klaus et al. |
| 2006/0258660 | A1 | 11/2006 | Guenzler-Pukall et al. |
| 2006/0258702 | A1 | 11/2006 | Guenzler-Pukall et al. |
| 2006/0270699 | A1 | 11/2006 | Guenzler-Pukall et al. |

FOREIGN PATENT DOCUMENTS

| DE | EP 0878 480 | * 11/1998 |
| EP | 0 650 961 B1 | 3/1997 |
| JP | 2002-322068 A | 11/2001 |
| WO | WO 99/21860 A1 | 5/1999 |
| WO | WO-02/074249 A2 | 9/2002 |
| WO | WO 02/074981 A2 | 9/2002 |
| WO | WO 03/045440 A1 | 6/2003 |
| WO | WO-03/049686 | 6/2003 |
| WO | WO 03/049686 A2 | 6/2003 |
| WO | WO-03/053997 A2 | 7/2003 |
| WO | WO 03/080566 A2 | 10/2003 |
| WO | WO-03/100438 A1 | 12/2003 |

OTHER PUBLICATIONS

Azevedo et al. (1995) Diabetes 44:695-698.
Bickel et al. (1998) Hepatology 28:404-411.
Bruick and McKnight (2001) Science 294:1337-1340.
DCCT Research Group (1993) New Eng J Med 329:977-986.
Epstein et al. (2001) Cell 107:43-54.
Franklin et al. (1991) Biochem Soc Trans 19:812-815.
Franklin et al. (2001) Biochem J 353:333-338.
Friedman et al. (2000) Proc Natl Acad Sci USA 97:4736-4741.
Ivan et al. (2001) Science 292:464-468.
Ivan et al. (2002) Proc Natl Acad Sci USA 99:13459-13464.
Jaakkola et al. (2001) Science 292:468-472.
Jia et al. (1994) Proc Natl Acad Sci USA 91:7227-7231.
Kaule and Gunzler (1990) Anal Biochem 184:291-297.
Kivirikko and Myllyharju (1998) Matrix Biol 16:357-368.
Lee et al. (2003) High Alt Med Biol 4:81-91.
Majamaa et al. (1984) Eur J Biochem 138:239-245.
Majamaa et al. (1985) Biochem J 229:127-133.
Myllyharju and Kivirikko (1997) EMBO J 16:1173-1180.
Thornburg et al. (1993) Biochemistry 32:14023-14033.
UKPDS Group (1998) Lancet 352:837-853.
Dorman et al. (1984) Diabetes 33:271-276.
Semenza, et al., "Transcriptional Regulation of Genes Encoding Glycolytic Enzymes by Hypoxia-inducible Factor 1," J Biol Chem, 269: 23757-23763 (1994).
Semenza, "HIF-1: mediator of physiological and pathophysiological responses to hypoxia", Institute of Genetic Medicine, Departments of Pediatrics and Medicine, J. Appl Physiol, 88:1474-1480 (2000).
Asikainen, et al., "Activation of hypoxia-inducible factors in hyperoxia through prolyl 4-hydroxylase blockade in cells and explants of primate lung" PNAS, 102:10212-10217 (2005).
Wright, et al, "Activation of the Prolyl Hydroxylase Oxygen-senor Results in Induction of GLUT1, Heme Oxygenase-1, and Nitric-oxide Synthase Proteins and Confers Protection from Metabolic Inhibition to Cardiomyocytes" J Biol Chem 278:20235-20239 (2003).
Ouiddir, et al., "Hypoxia Upregulates Activity and Expression of the Glucose Transporter GLUT1 in Alveolar Epithelial Cells" Am J. Respir Cell Mol Biol 21: 710-718 (1999).
Almansa, Carmen, et al., "2,2-Dialkylnaphthalen-1-ones as New Potassium Channel Activators," J. Med. Chem. (1993) 36(15): 2121-2138.
Finch, N., et al., "Synthesis and Antihypertensive Activity of 5-amino-2-pyridinecarboxylic Acid Derivatives," J. Med. Chem. (1980) 23(12):1405-1410.
Marfella, R., et al., "Myocardial Infarction in Diabetic Rats: Role of Hyperglycaemia on Infarct Size and Early Expression of Hypoxia-Inducible Factor 1," Diabetoiogia (2002) 45:1172-1181.
Yun, Zhong, et al., "Inhibition of *PPARγ2* Gene Expression by the HIF-1-Regulated Gene *DEC1/ Stra13*: A Mechanism for Regulation of Adipogenesis by Hypoxia," Dev. Cell (2002) 2:331-341.

* cited by examiner

*Primary Examiner* — Christopher R. Tate
*Assistant Examiner* — Roy Teller
(74) *Attorney, Agent, or Firm* — Leanne C. Price; Paul E. Borchardt

(57) ABSTRACT

The present invention relates to methods and compounds for regulating glucose metabolism, achieving glucose homeostasis, and decreasing blood glucose levels. Methods and compounds for treating or preventing diabetes, hyperglycemia, and disorders and conditions associated with altered or impaired glucose metabolism are also provided.

15 Claims, 12 Drawing Sheets

A.

B.

A.

B.

A.

B.

Compound B (20 mg/kg)

Compound B (100 mg/kg)

A.

B.

C.

A.

B.

SEQUENCE LISTING

```
<160> NUMBER OF SEQ ID NOS: 5

<210> SEQ ID NO 1
<211> LENGTH: 23
<212> TYPE: DNA
<213> ORGANISM: Mus musculus

<400> SEQUENCE: 1
cccaggagga gagagatccg att                                            23

<210> SEQ ID NO 2
<211> LENGTH: 23
<212> TYPE: DNA
<213> ORGANISM: Mus musculus

<400> SEQUENCE: 2
aggtccctgg ctagtgcttc aga                                            23
```

```
<210> SEQ ID NO 3
<211> LENGTH: 22
<212> TYPE: DNA
<213> ORGANISM: Rattus rattus

<400> SEQUENCE: 3
taggcacggc gactaccatc ga                                              22

<210> SEQ ID NO 4
<211> LENGTH: 23
<212> TYPE: DNA
<213> ORGANISM: Rattus rattus

<400> SEQUENCE: 4
cggcggcttt ggtgactcta gat                                             23

<210> SEQ ID NO 5
<211> LENGTH: 19
<212> TYPE: PRT
<213> ORGANISM: Homo sapiens

<400> SEQUENCE: 5

Asp Leu Asp Leu Glu Met Leu Ala Pro Tyr Ile Pro Met Asp Asp Asp
1               5                   10                  15

Phe Gln Leu
```

TREATMENT OF DIABETES

This application claims the benefit of U.S. Provisional Application Ser. No. 60/431,351, filed on 6 Dec. 2002; U.S. Provisional Application Ser. No. 60/476,331, filed on 6 Jun. 2003; and U.S. Provisional Application Ser. No. 60/476,726, filed on 6 Jun. 2003, each of which is incorporated by reference herein in its entirety.

FIELD OF THE INVENTION

The present invention relates to glucose regulation and homeostasis, and to treatment or prevention of disorders such as diabetes associated with impaired glucose regulation.

BACKGROUND OF THE INVENTION

Diabetes mellitus, more commonly known as diabetes, is a disease characterized by hyperglycemia due to defective insulin secretion, insulin action, or both. Type 1 diabetes (previously known as insulin dependent diabetes mellitus (IDDM)) is an auto-immune disease that affects the islets of Langerhans, destroying the body's ability to produce insulin. Type I diabetes represents 10% of all diabetes cases and affects as many as 1 million people in the United States. Type 2 diabetes (previously known as non-insulin dependent diabetes mellitus (NIDDM)) is a metabolic disorder resulting from the body's inability to produce enough insulin or properly use the insulin produced. Roughly 90% of all diabetic individuals in the United States suffer from Type 2 diabetes. Type 1 and Type 2 diabetes are metabolic disorders characterized by hyperglycemia due to defective insulin secretion, insulin action, or both.

The prevalence of diabetes is increasing at an alarming rate. Between 1976 and 1994, diabetes among adults in the United States increased from 8.9% to 12.3% of the population. There are currently approximately 16 million people (6% of the population) in the United States who suffer from diabetes and roughly 800,000 people will be diagnosed with diabetes this year. (Harris et al. (1998) Diabetes Care 21:518-5241; Nathan (2002) N Engl J Med 347:1342-1349.) Diabetes can be associated—prior to, during, or after onset—with a wide range of conditions and complications affecting various organs throughout the body; for example, various microvascular diseases and other disorders, including, e.g., retinopathy, nephropathy, neuropathy, etc., leading to blindness, kidney failure, etc. Diabetes can severely compromise quality of life and can even be fatal. Therefore, there is a need in the art for effective means of treating and preventing the development and progression of diabetes and associated complications.

Several risk factors are associated with diabetes in general, and with the development of Type 2 diabetes in particular, such as a family history of diabetes, certain ethnic or racial groups, a history of gestational diabetes, obesity, in particular, high levels of visceral or abdominal fat, a sedentary lifestyle, age, high blood pressure, schizophrenia, etc., as well as altered glucose metabolism, including impaired glucose tolerance (IGT) or prediabetes. Therefore, there is a need in the art for effective means of treating and preventing the development and progression of risk factors associated with diabetes.

Conditions such as diabetes are associated with a loss in control of glucose regulation. Diabetic and hyperglycemic conditions can lead to development of, can develop in response to, or can otherwise be associated with various conditions and disorders including atherosclerosis, vascular disorders, e.g., stroke, etc., obesity, cardiac disease, e.g., congestive heart failure (CHF), myocardial infarction (MI), and downstream effects, etc., or with risk factors associated with these conditions and disorders. There is thus a need in the art for treating or preventing or for minimizing the risks of development of these conditions in association with diabetes or hyperglycemia. The present methods answer this need by providing a pharmacological approach that effectively permits administration of a single compound that targets a family of associated processes and achieves coordinated effects, in contrast to current approaches, in which different conditions and different aspects of different conditions can involve the application of multiple therapeutic approaches in order to achieve the desired therapeutic effects.

Current treatments for diabetes seek to control glucose levels in the blood (e.g., to achieve glycemic control), attempting to reproduce natural physiological glucose homeostasis. While lifestyle changes, e.g., controlled diet and increased exercise, can be recommended, this approach is limited in its effectiveness. Such lifestyle modifications might not prevent or counter the development of contributing physiological factors, and might delay, but not prevent, the progression of the disease. Additionally, lack of patient compliance can limit the effectiveness of this approach.

A common therapeutic approach involves treatment with insulin, e.g., through a course of injections that need to be administered in a carefully scheduled fashion, often requiring daily or even multiple daily injections. Treatments requiring injections of insulin carry with them associated risks of hypoglycemia and hyperinsulinemia. Further, the success of such treatments is often compromised by lack of patient compliance, i.,e., failure to follow the recommended treatment schedule. Additional insulin-based therapies, e.g., administration of insulin secretagogues (compounds that stimulate insulin release from the pancreas), similarly carry the risk of inducing hypoglycemia, etc. These therapies, and available treatments, e.g., PPAR-gamma agonist therapy, etc., are associated with other effects, for example, weight gain, a risk factor for diabetes in and of itself. Therefore, there is a need for methods and compounds for effectively treating or preventing diabetes, hyperglycemia, and associated risk factors for diabetes, such as weight gain and obesity, that offer improved ease of administration and that are not associated with development of or risk for development of other factors associated with diabetes, e.g., weight gain, etc. There is a need for a therapeutic approach to diabetes and related conditions that more closely mimics the body's own physiological mechanisms for achieving glucose homeostasis. There is a need for courses of treatment that have improved ease of administration, increasing patient comfort as well as the likelihood of patient compliance. Additionally, there is a need for treatments for diabetes or associated conditions, which treatments are not associated with effects that exacerbate or worsen the condition being treated.

Glucose metabolism, e.g., the synthesis, processing, and utilization of glucose, etc., is essential to maintaining proper glucose balance and homeostasis. A disruption in glucose metabolism or glucose regulation can lead to a disruption in glucose homeostasis, resulting in disproportionately high levels (i.e., hyperglycemia) or low levels (i.e., hypoglycemia) of blood glucose. Hyperglycemia and hypoglycemia affect quality of life and, in chronic or severe forms, produce neurological and vascular damage. There is thus a need for effective methods for regulating glucose metabolism and homeostasis (e.g., achieving glycemic control), and for methods for treating or preventing conditions and disorders associated with altered or impaired glucose metabolism and homeostasis, such as, e.g., diabetes, hyperglycemia, etc.

The present invention meets these needs by providing methods for treating or preventing diabetes, hyperglycemia, and associated disorders and risk factors. The present methods offer improvements over existing therapies by offering a coordinated therapeutic approach and improved routes of administration, and eliminating undesirable side effects associated with some treatments, e.g., weight gain, etc. Methods for regulating glucose metabolism and achieving glycemic control are also provided.

SUMMARY OF THE INVENTION

The present invention relates to methods and compounds for regulating glucose metabolism and achieving glucose homeostasis. Methods for decreasing blood glucose levels, reducing insulin resistance, decreasing glycated hemoglobin levels, and improving glycemic control in a subject are also provided. Methods for treating or preventing diabetes, hyperglycemia, and other conditions associated with increased blood glucose levels are provided, as are methods for treating or preventing conditions associated with diabetes, e.g., conditions that are risk factors for or that develop in parallel with or as a result of diabetes.

In various embodiments, the subject is a cell, tissue, or organ. In other embodiments, the subject is an animal, preferably a mammal, most preferably a human. When the subject is a cell, the invention specifically contemplates that the cell can be an isolated cell, either prokaryotic or eukaryotic. In the case that the subject is a tissue, the invention specifically contemplates both endogenous tissues and in vitro tissues, e.g., tissues grown in culture. In preferred embodiments, the subject is an animal, particularly, an animal of mammalian species including rat, rabbit, bovine, ovine, porcine, murine, equine, and primate species. In a most preferred embodiment, the subject is human.

The present invention provides methods for regulating glucose metabolism. In one aspect, the present methods comprise regulating glucose metabolism in a subject by stabilizing HIFα in the subject, thus regulating glucose metabolism in the subject. In various aspects, HIFα is HIF1α, HIF2α, or HIF3α. In a preferred aspect, stabilizing HIFα comprises administering to the subject an effective amount of a compound that inhibits HIF hydroxylase activity.

Stabilization of HIFα can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc, or a polynucleotide encoding such a variant. In other aspects, the present invention contemplates that stabilizing HIFα comprises administering an agent that stabilizes HIFα. The agent can be composed of polynucleotides, e.g. antisense sequences; polypeptides; antibodies; other proteins; carbohydrates; fats; lipids; and organic and inorganic substances, e.g., small molecules, etc. In a preferred embodiment, the present invention contemplates stabilizing HIFα, e.g., in a subject, by administering to the subject an agent that stabilizes HIFα wherein the agent is a compound, e.g., small molecule compound, etc., that stabilizes HIFα.

The invention further contemplates methods for regulating glucose metabolism in a subject by administering to the subject an effective amount of a compound of the invention, thus regulating glucose metabolism in the subject. In a preferred aspect, a compound of the invention is a compound that inhibits HIF hydroxylase activity. In a most preferred aspect, a compound of the invention is a compound that inhibits HIF prolyl hydroxylase activity. In another preferred aspect, the HIF hydroxylase is selected from the group consisting of EGLN1, EGLN2, and EGLN3.

The invention further provides methods for regulating a glucose metabolic process in a subject by stabilizing HIFα in a subject, or by administering to the subject an effective amount of a compound of the invention, thereby regulating the glucose metabolic process in the subject. In various embodiments, the glucose metabolic process is selected from the group consisting of, e.g., glucose uptake, glucose transport, glucose storage, glucose processing, glucose utilization, and glucose synthesis, etc., In particular embodiments, the present invention contemplates methods for altering expression of a glucose regulatory factor in a subject by stabilizing HIFα in a subject, or by administering to the subject an effective amount of a compound of the invention, thereby altering expression of the glucose regulatory factor in the subject.

In one embodiment, the present invention provides a method for increasing expression of a glucose regulatory factor in a subject, by stabilizing HIFα in the subject or by administering to the subject an effective amount of a compound of the invention, thereby increasing expression of the glucose regulatory factor in the subject. In further embodiments, the glucose regulatory factor is selected from the group consisting of PFK-P, PFK-L, enolase-1, GluT-1, lactate dehydrogenase, aldolase-1, hexokinase-1, IGFBP-1, and IGF. In a particular aspect, the increase in expression of the glucose regulatory factor is a sustained increase. In one aspect, the glucose regulatory factor is a glycolytic factor. In a further aspect, the glycolytic factor is selected from the group consisting of PFK-P, PFK-L, enolase-1, lactate dehydrogenase, aldolase-1, and hexokinase-1.

The present invention provides methods for achieving glucose homeostasis in a subject. In one aspect, the present methods comprise achieving glucose homeostasis in a subject by stabilizing HIFα in the subject, thereby achieving glucose homeostasis in the subject. In another aspect, the present methods comprise achieving glucose homeostasis in a subject by administering to the subject an effective amount of a compound of the invention, thereby achieving glucose homeostasis in the subject.

The present invention provides methods for decreasing blood glucose levels in a subject. In one aspect, the present methods comprise decreasing blood glucose levels in a subject by stabilizing HIFα in the subject, thereby decreasing blood glucose levels in the subject. In another aspect, the present methods comprise decreasing blood glucose levels in a subject by administering to the subject an effective amount of a compound of the invention, thereby decreasing blood glucose levels in the subject.

The present invention provides methods for decreasing glycated hemoglobin levels in a subject. In one aspect, the present methods comprise decreasing glycated hemoglobin levels in a subject by stabilizing HIFα in the subject, thereby decreasing glycated hemoglobin levels in the subject. In another aspect, the present methods comprise decreasing glycated hemoglobin levels in a subject by administering to the subject an effective amount of a compound of the invention, thereby decreasing glycated hemoglobin levels in the subject.

Methods for treating or preventing diabetes in a subject having or at risk for having/developing diabetes are encompassed herein. In one embodiment, the methods comprise treating or preventing diabetes in a subject having or at risk for having diabetes by stabilizing HIFα in the subject, thereby preventing or treating diabetes. In another embodiment, the present methods comprise treating or preventing diabetes in a subject by administering to the subject an effective amount of a compound of the invention, thereby treating or preventing diabetes in the subject.

The invention further provides methods for treating or preventing a disorder associated with increased blood glucose levels in a subject. In one embodiment, the methods comprise treating or preventing a disorder associated with increased blood glucose levels in a subject by stabilizing HIFα in the subject, thereby preventing or treating the disorder associated with increased blood glucose levels. In another embodiment, the present methods comprise treating or preventing a disorder associated with increased blood glucose levels in a subject by administering to the subject an effective amount of a compound of the invention, thereby treating or preventing a disorder associated with increased blood glucose levels in the subject. In various embodiments, the disorder is selected from the group consisting of diabetes, hyperglycemia, obesity, impaired glucose tolerance, hypertension, retinopathy, neuropathy, nephropathy, hyperlipidemia, and vascular disease.

The invention also contemplates methods for treating or preventing a condition associated with diabetes in a subject. In one embodiment, the methods comprise treating or preventing a condition associated with diabetes in a subject by stabilizing HIFα in the subject, thereby treating or preventing the condition associated with diabetes in the subject. In another embodiment, the present methods comprise treating or preventing a condition associated with diabetes in a subject by administering to the subject an effective amount of a compound of the invention, thereby treating or preventing the condition associated with diabetes in the subject. In various embodiments, the disorder is selected from the group consisting of hypertension, obesity, hyperglycemia, impaired glucose tolerance, hyperlipidemia, nephropathy, neuropathy, retinopathy, atherosclerosis, and vascular disease. In one embodiment, the subject is a subject having diabetes. In another embodiment, the subject is a subject at risk for having diabetes.

The present invention provides methods for decreasing blood triglyceride levels in a subject. In one aspect, the present methods comprise decreasing blood triglyceride levels in a subject by stabilizing HIFα in the subject, thereby decreasing blood triglyceride levels in the subject. In another aspect, the present methods comprise decreasing blood triglyceride levels in a subject by administering to the subject an effective amount of a compound of the invention, thereby decreasing blood triglyceride levels in the subject.

The present invention provides methods for reducing insulin resistance in a subject. In one aspect, the present methods comprise reducing insulin resistance in a subject by stabilizing HIFα in the subject, thereby reducing insulin resistance in the subject. In another aspect, the present methods comprise reducing insulin resistance levels in a subject by administering to the subject an effective amount of a compound of the invention, thereby reducing insulin resistance in the subject.

The present invention provides methods for increasing glycemic control in a subject. In one aspect, the present methods comprise increasing glycemic control in a subject by stabilizing HIFα in the subject, thereby increasing glycemic control in the subject. In another aspect, the present methods comprise increasing glycemic control in a subject by administering to the subject an effective amount of a compound of the invention, thereby increasing glycemic control in the subject. In a further aspect, the subject is a subject having hyperglycemia.

In various embodiments, the present invention provides formulations or medicaments or pharmaceutical compositions comprising the compounds of the invention, and methods for the manufacture and use of such formulations or medicaments or pharmaceutical compositions.

DESCRIPTION OF THE INVENTION

Figure 1:
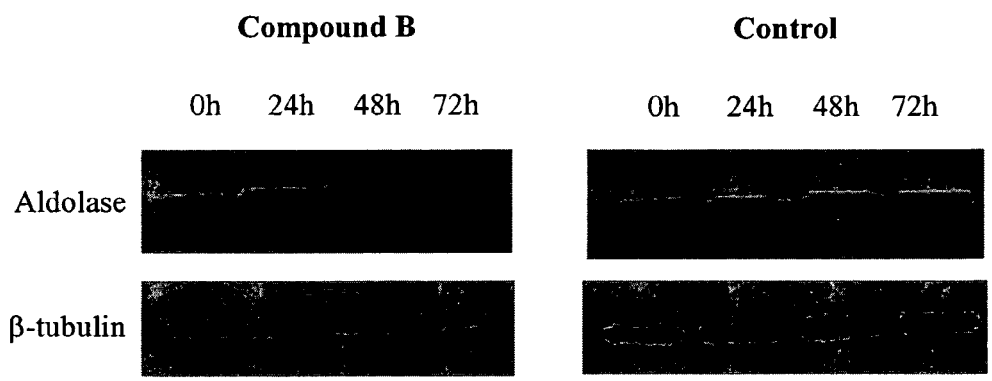
FIGS. 1A and 1B show induction of aldolase and glucose tranporter-1 (GluT-1) in cells treated with compounds of the invention.
Figure 1:
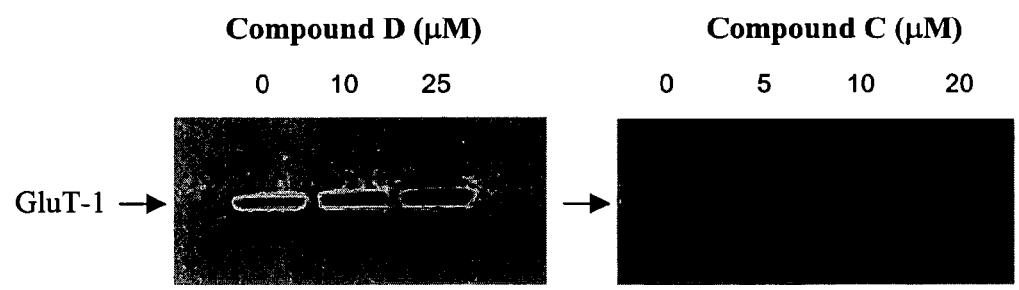

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments, a reference to a "compound" is a reference to one or more compounds and to equivalents thereof as described herein and as known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

Definitions

The term "glucose regulation" or "regulation of glucose metabolism" as used herein refer to processes by which a cell, tissue, organ, organ system, or whole organism maintains glucose homeostasis by altering, e.g., increasing or decreasing, specific processes of glucose metabolism. Glucose metabolism or glucose metabolic processes encompass processes involving glucose synthesis, processing, transport, uptake, utilization, or storage, and includes gluconeogenesis and glycolysis. Specific aspects of glucose metabolism and regulation include expression of glucose transporters or enzymes which facilitate movement of glucose across a cell membrane and retention or secretion of glucose by a cell; alteration in expression and/or activity of enzymes involved in glucose utilization or formation, including, e.g., glycolytic and gluconeogenic enzymes; and alteration of glucose distribution within body or culture fluids, including, e.g., interstitial (i.e. extracellular) and intracellular fluids, blood, urine, and the like.

The term "glucose homeostasis" refers to maintenance of normal glucose levels, in particular, normal blood glucose levels, in an organism.

The term "glycemic control" refers to maintaining, restoring, or achieving normal or near normal blood glucose levels. Glycemic control can also refer to normalization of glycated hemoglobin levels in an organism.

The terms "metabolic condition" and "metabolic disorder" are used interchangeably and refer to any disorder associated with or aggravated by impaired or altered glucose regulation or glycemic control, such as, for example, insulin resistance. Such disorders include, but are not limited to, diabetes, hyperglycemia, obesity, etc.

The term "hyperglycemia" as used herein refers generally to blood glucose levels that are above normal. Hyperglycemia can be determined by any measure accepted and utilized by those of skill in the art. Currently, in humans, normal blood glucose is considered to be between about 70 and 120 mg/dl, but varies depending on the fasting state. Before a meal, blood glucose can range from about 80 to 120 mg/dl, whereas two hours after a meal, blood glucose can be at or below about 180 mg/dl. Additionally, in fasted individuals, normal blood glucose is below about 110 mg/dl. A subject having a blood glucose value of about 126 mg/dl or greater is generally considered hyperglycemic, and a subject whose blood glucose is above about 200 mg/dl is generally considered diabetic.

The term "obesity" refers to excess fat in the body. Obesity can be determined by any measure accepted and utilized by those of skill in the art. Currently, an accepted measure of obesity is body mass index (BMI), which is a measure of body weight in kilograms relative to the square of height in meters. Generally, for an adult over age 20, a BMI between about 18.5 and 24.9 is considered normal, a BMI between about 25.0 and 29.9 is considered overweight, a BMI at or above about 30.0 is considered obese, and a BMI at or above about 40 is considered morbidly obese. (See, e.g., Gallagher et al. (2000) Am J Clin Nutr 72:694-701.) These BMI ranges are based on the effect of body weight on increased risk for disease. Some common conditions related to overweight and obesity include cardiovascular disease, high blood pressure (i.e., hypertension), osteoarthritis, cancer, and diabetes. Although BMI correlates with body fat, the relation between BMI and actual body fat differs with age and gender. For example, women are more likely to have a higher percent of body fat than men for the same BMI.

Another measure of obesity is body-fat percentage. Various methods are available for indirectly measuring body fat, including skin-fold measurement, hydrodensitometry, bioelectrical impedance analysis (BIA), dual-energy X-ray absorptiometry, total-body potassium measurement, and in vivo neutron activation analysis. Hydrodensitometry, or hydrostatic weighing (HW), determines total body volume by measuring the difference between a subject's weight in water and in air. Similarly, air-displacement plethysmography (AP) determines total body volume by measuring the reduction in chamber volume caused by introducting a subject into a chamber with a fixed air volume. Whole-body density and body composition are then calculated using validated prediction equations. BIA estimates body resistance, or impedance, from a voltage drop initiated from a small current passed between electrodes. The level of impedance, an indication of the water and electrolyte composition of the body, is then used to estimate lean tissue content and body water volume from developed regression equations. Assuming a hydration fraction of lean tissue, additional regression equations are used to estimate lean body mass and fat mass. The percentage of body fat in women should generally be about 17 to 27 percent, although up to about 31 percent is considered acceptable. In men, the body fat percentage should generally be about 10 to 20 percent, although up to about 25 percent is considered acceptable.

The term "HIFα" refers to the alpha subunit of hypoxia inducible factor protein. HIFα may be any human or other mammalian protein, or fragment thereof, including human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130 and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and cow HIF-1α (Genbank Accession No. BAA78675). HIFα may also be any non-mammalian protein or fragment thereof, including *Xenopus laevis* HIF-1α (Genbank Accession No.

CAB96628), *Drosophila melanogaster* HIF-1α (Genbank Accession No. JC4851), and chicken HIF-1α (Genbank Accession No. BAA34234). HIFα gene sequences may also be obtained by routine cloning techniques, for example by using all or part of a HIFα gene sequence described above as a probe to recover and determine the sequence of a HIFα gene in another species.

Fragments of HIFα include the regions defined by human HIF-1α from amino acid 401 to 603 (Huang et al., supra), amino acid 531 to 575 (Jiang et al. (1997) J Biol Chem 272:19253-19260), amino acid 556 to 575 (Tanimoto et al., supra), amino acid 557 to 571 (Srinivas et al. (1999) Biochem Biophys Res Commun 260:557-561), and amino acid 556 to 575 (Ivan and Kaelin (2001) Science 292:464-468). Further, a fragment of HIFα includes any fragment containing at least one occurrence of the motif LXXLAP, e.g., as occurs in the HIFα native sequence at $L_{397}$TLLAP and $L_{559}$EMLAP. Additionally, a fragment of HIFα includes any fragment retaining at least one functional or structural characteristic of HIFα For example, a HIF peptide for use in the screening assay of Example 14 may comprise DLDLEMLAPYIPMDDDFQL (SEQ ID NO:5).

The term "HIF hydroxylase" refers to any enzyme that is capable of hydroxylating an amino acid residue in the HIF protein, particularly the HIFα subunit. Preferably, the amino acid residue is a proline and/or an asparagine residue.

The term "HIF asparaginyl hydroxylase" refers to any enzyme that is capable of hydroxylating an asparagine residue in the HIF protein. Preferaably, the asparagine residue hydroxylated by HIF asparaginyl hydroxylase includes, e.g., the $N_{803}$ residue of HIF-1α or a homologous asparagine residue in another HIFα isoform. HIF asparaginyl hydroxylase includes Factor Inhibiting HIF (FIH), an asparaginyl hydroxylase responsible for regulating transactivation of HIFα (GenBank Accession No. AAL27308; Mahon et al. (2001) Genes Dev 15:2675-2686; Lando et al. (2002) Science 295:858-861; and Lando et al. (2002) Genes Dev 16:1466-1471. Also, see, Elkins et al. (2002) J Biol Chem C200644200.)

The terms "HIF prolyl hydroxylase" and "HIF PH" refer to any enzyme that is capable of hydroxylating a proline residue in the HIF protein. Preferably, the proline residue hydroxylated by HIF PH includes the proline found within the motif LXXLAP, e.g., as occurs in the human HIF-1α native sequence at $L_{397}$TLLAP and $L_{559}$EMLAP. HIF PH includes members of the Egl-Nine (EGLN) gene family described by Taylor (2001,Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340). Examples of HIF PH enzymes include human SM-20 (EGLN1) (GenBank Accession No. AAG33965; Dupuy et al. (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA19321). Additionally, HIF PH may include *Caenorhabditis elegans* EGL-9 (GenBank Accession No. AAD56365) and *Drosophila melanogaster* CG1114 gene product (GenBank Accession No. AAF52050). HIF PH also includes any active fragment of the foregoing full-length proteins.

A "sample" as used herein may be derived from any source, for example, from bodily fluids, secretions, tissues, cells, or cells in culture including, but not limited to, saliva, blood, urine, serum, plasma, vitreous, synovial fluid, cerebral spinal fluid, amniotic fluid, and organ tissue (e.g., biopsied tissue); from chromosomes, organelles, or other membranes isolated from a cell; from genomic DNA, cDNA, RNA, mRNA, etc.; and from cleared cells or tissues, or blots or imprints from such cells or tissues. Samples may be derived from any source, such as, for example, a human subject, or a non-human mammalian subject, etc. Also contemplated are samples derived from any animal model of disease. A sample can be in solution or can be, for example, fixed or bound to a substrate. A sample can refer to any material suitable for testing for the presence of transcripts or proteins associated with metabolic regulation; or for measuring fat and glucose levels. Methods for obtaining such samples are within the level of skill in the art.

A "subject" as used herein may include isolated cells, either prokaryotic or eukaryotic, or tissues grown in culture. Preferably, subjects include animals, particularly a mammalian species including rat, rabbit, bovine, ovine, porcine, murine, equine, and primate, particularly human.

Invention

The present invention provides methods and compounds for treating or preventing diabetes, hyperglycemia, and other conditions associated with altered or impaired glucose metabolism and/or homeostasis. Methods and compounds useful for treating, preventing, or delaying the development and/or progression of conditions associated with diabetes and other conditions associated with altered or impaired glucose metabolism are also provided, as are methods and compounds for regulating glucose metabolism and achieving glucose homeostasis.

The invention relates to the discovery that stabilization of the alpha subunit of hypoxia inducible factor (HIFα) leads to a decrease in blood glucose levels. The invention further relates to the discovery that stabilization of HIFα regulates glucose metabolism. Additionally, the invention further relates to the discovery that the compounds of the invention can be used to decrease blood glucose levels, regulate glucose metabolism, and achieve glucose homeostasis.

Hypoxia inducible factor (HIF) is a physiological factor involved in multiple biological pathways. HIFα is degraded under normoxic or normal oxygen conditions. Under hypoxic or low oxygen conditions, HIFα is stabilized to produce a number of downstream effects. It was recently determined that hydroxylation of particular residues on the HIFα subunit targeted HIFα for degradation, thus preventing the formation of stable HIF complex under normal oxygen conditions, and that the hydroxylation was determined to result from the activity of certain HIF hydroxylase enzymes. (See, e.g., Ivan and Kaelin (2001) Science 292:464-468; Jaakkola et al. (2001) Science 292:468-472; Epstein et al (2001) Cell 107: 43-54; and Bruick and McKnight (2001) Science 294:1337-1340.) These HIF hydroxylase enzymes belong to the 2-oxoglutarate dioxygenase enzyme family. These enzymes are oxygen-dependent and, under low oxygen or hypoxic conditions, the hydroxylation of HIFα residues is inhibited. Therapeutic stabilization of HIFα, and stabilization of HIFα through inhibition of hydroxylation of HIFα, have been previously described. (See, e.g., International Publication No. WO 03/049686, incorporated herein by reference in its entirety.)

Methods

In one aspect, the present invention provides methods for decreasing blood glucose levels or for regulating glucose metabolism by stabilizing the alpha subunit of hypoxia inducible factor (HIFα) in a subject. In a further aspect, the methods comprise decreasing blood glucose levels or regulating glucose metabolism by inhibiting the hydroxylation of HIFα in a subject. In a preferred aspect, the methods of the present invention encompass methods for decreasing blood glucose levels or regulating glucose metabolism by inhibiting the activity of a HIF hydroxylase enzyme in a subject. In a most preferred aspect, the methods comprise decreasing blood glucose levels or regulating glucose metabolism by inhibiting the activity of a HIF prolyl hydroxylase enzyme.

Stabilization of HIFα can be accomplished by any of the methods available to and known by those of skill in the art, and can involve use of any agent that interacts with, binds to, or modifies HIFα or factors that interact with HIFα, including, e.g., enzymes for which HIFα is a substrate. In certain aspects, the present invention contemplates providing a constitutively stable HIFα variant, e.g., stable HIF muteins, etc., or a polynucleotide encoding such a variant. (See, e.g., U.S. Pat. Nos. 6,562,799 and 6,124,131; and U.S. Pat. No. 6,432,927.) In other aspects, the present invention contemplates that stabilizing HIFα comprises administering an agent that stabilizes HIFα. The agent can be composed of polynucleotides, e.g. antisense sequences (see, e.g., International Publication No. WO 03/045440); polypeptides; antibodies; other proteins; carbohydrates; fats; lipids; and organic and inorganic substances, e.g., small molecules, etc. In a preferred embodiment, the present invention contemplates stabilizing HIFα, e.g., in a subject, by administering to the subject an agent that stabilizes HIFα wherein the agent is a compound, e.g., small molecule compound, etc., that stabilizes HIFα.

In other embodiments, the methods of the invention comprise stabilizing HIFα by inhibiting the activity of at least one enzyme selected from 2-oxoglutarate dioxygenase family. In a preferred embodiment, the enzyme is a HIF hydroxylase enzyme, e.g., EGLN-1, EGLN-2, EGLN-3, etc. (See, e.g., Taylor (2001) Gene 275:125-132; Epstein et al. (2001) Cell 107:43-54; and Bruick and McKnight (2001) Science 294: 1337-1340.) It is specifically contemplated, however, that the enzyme be any enzyme selected from the 2-oxoglutarate dioxygenase enzyme family, including, for example, procollagen lysyl hydroxylase, procollagen prolyl 3-hydroxylase, procollagen prolyl 4-hydroxylase α(I) and α(II), thymine 7-hydroxylase, aspartyl (asparaginyl) β-hydroxylase, ε-N-trimethyllysine hydroxylase, and γ-butyrobetaine hydroxylase, etc. (See, e.g., Majamaa et al. (1985) Biochem J 229: 127-133; Myllyharju and Kivirikko (1997) EMBO J 16:1173-1180; Thornburg et al. (1993) 32:14023-14033; and Jia et al. (1994) Proc Natl Acad Sci USA 91:7227-7231.)

In certain embodiments, the methods comprise decreasing blood glucose levels or regulating glucose metabolism by inhibiting the hydroxylation of certain residues of HIFα, e.g., proline residues, asparagine residues, etc. In a preferred embodiment, the residues are proline residues. In specific embodiments, the residues can be the $P_{564}$ residue in HIF-1α or a homologous proline in another HIFα isoform, or the $P_{402}$ residue in HIF-1α or a homologous proline in another HIFα isoform, etc. In other embodiments, the present methods may encompass inhibiting hydroxylation of HIFα asparagine residues, e.g., the $N_{803}$ residue of HIF-1α or a homologous asparagine residue in another HIFα isoform.

Compounds

In one aspect, the present invention provides methods for decreasing blood glucose levels or regulating glucose metabolism by administering a compound of the invention to a subject. A compound of the invention is any compound that inhibits or otherwise modulates the activity of a 2-oxoglutarate dioxygenase enzyme. 2-oxoglutarate dioxygenase enzymes include, but are not limited to, hydroxylase enzymes. Hydroxylase enzymes hydroxylate target substrate residues and include, for example, prolyl, lysyl, asparaginyl (asparagyl, aspartyl) hydroxylases, etc. Hydroxylases are sometimes described by target substrate, e.g., HIF hydroxylases, procollagen hydroxylases, etc., and/or by targeted residues within the substrate, e.g., prolyl hydroxylases, lysyl hydroxylases, etc., or by both, e.g., HIF prolyl hydroxylases, procollagen prolyl hydroxylases, etc. Representative 2-oxoglutarate dioxygenase enzymes include, but are not limited to, HIF hydroxylases, including HIF prolyl hydroxylases, e.g., EGLN1, EGLN2, and EGLN3, HIF asparaginyl hydroxylases, e.g., factor inhibiting HIF (FIH), etc.; procollagen hydroxylases, e.g., procollagen lysyl hydroxylases, procollagen prolyl hydroxylases, e.g., procollagen prolyl 3-hydroxylase, procollagen prolyl 4-hydroxylase α(I) and α(II), etc.; thymine 7-hydroxylase; aspartyl (asparaginyl) β-hydroxylase; ε-N-trimethyllysine hydroxylase; γ-butyrobetaine hydroxylase, etc. Although enzymatic activity can include any activity associated with any 2-oxoglutarate dioxygenase, the hydroxylation of amino acid residues within a substrate is specifically contemplated. Although hydroxylation of proline and/or asparagine residues within a substrate is specifically included, hydroxylation of other amino acids is also contemplated.

In certain embodiments, a compound of the invention is a compound that inhibits hydroxylase activity. In preferred embodiments, a compound of the invention is a compound that inhibits HIF hydroxylase activity. In various embodiments, the activity is due to a HIF prolyl hydroyxase, such as, for example, EGLN1, EGLN2, or EGLN3, etc. In other embodiments, the activity is due to a HIF asparaginyl hydroxylase, such as, for example, including, but not limited to, FIH.

In one aspect, a compound of the invention that shows inhibitory activity toward one or more 2-oxoglutarate dioxygenase enzyme may also show inhibitory activity toward one or more additional 2-oxoglutarate dioxygenase enzymes, e.g., a compound that inhibits the activity of a HIF hydroxylase may additionally inhibit the activity of a collagen prolyl hydroyxlase, a compound that inhibits the activity of a HIF prolyl hydroylxase may additionally inhibit the activity of a HIF asparaginyl hydroylxase, etc.

In one aspect, the present invention provides methods for decreasing blood glucose levels or regulating glucose metabolism by administering a compound of the invention to a subject. A compound of the invention is a small molecule compound that inhibits HIF hydroxylase activity. A preferred compound of the invention is a compound that inhibits HIF prolyl hydroxylase activity. The inhibition can be direct or indirect, can be competitive or non-competitive, etc. Exemplary compounds and methods for identifying additional compounds of the present invention are provided, infra.

Glucose

Under normal conditions, glucose serves as the body's principal energy source for peripheral tissues. Brain and other nervous tissue require glucose as a sole energy source under normal conditions, and require significant amounts of glucose even under stressful conditions, e.g., long-term fasting. The liver is the major organ that regulates blood glucose levels, preventing blood glucose levels from falling in periods of fasting by producing glucose from the breakdown of stored glycogen or by synthesis from precursors such as lactate, pyruvate, glycerol, and amino acids. Maintenance of glucose homeostasis, e.g., internal equilibrium of glucose, requires a balance between hepatic glucose production and peripheral glucose uptake and utilization.

Blood glucose homeostasis, the maintenance of an internal equilibrium of glucose, is closely controlled and affected by many biochemical factors, and encompasses a variety of processes. To achieve glucose homeostasis, the body regulates glucose at several levels, including glucose uptake, transport, storage, processing, synthesis, utilization, etc. Therefore, glucose homeostasis is affected by a number of factors, including, e.g., external factors, such as physical demand, food uptake, etc., and internal factors, such as circulating levels of insulin, glucagon, etc.

Increased Glucose Levels

Disruption in the normal regulation of glucose can lead to blood glucose levels deviating from, i.e., elevated or low compared to, normal blood glucose levels. Chronically elevated blood glucose levels, characteristic, for example, of hyperglycemia, diabetes, etc., can impose multiple detrimental effects on various organs, tissue, and systems of the body. Diabetes, hyperglycemia, or elevated blood glucose levels are associated with numerous disorders and conditions, including accelerated atherosclerosis, increased chronic heart disease, myocardial infarction, stroke, microangiopathy, damage to blood vasculature, peripheral vascular disease leading to decreased circulation in the arms and legs, macrovascular complication, ocular disorders, such as, for example, diabetic retinopathy, macular degeneration, cataracts, etc., kidney disorders, including, diabetic nephropathy, kidney damage, etc., damage to nerves and other neuropathies, including diabetic neuropathy, peripheral neuropathy, damage to nerves of the autonomic nervous system, etc., hyperinsulinaemia, hyperlipidaemia, insulin resistance, impaired glucose metabolism, impaired glucose tolerance, skin and connective tissue disorders, foot wounds and ulcerations, diabetic ketoacidosis, etc.

Altered or impaired glucose regulation, and the presence of or risk for development of disorders including diabetes, hyperglycemia, etc., can be identified by measurement of circulating glucose or determination of blood/plasma glucose levels. Blood glucose levels are most often measured by a fasting blood glucose test, a random blood glucose test, or an oral glucose tolerance test.

Blood glucose levels can be measured by a fasting blood glucose test. In such an analysis, measurements reflect that normal fasting (i.e., no food or liquid other than water for eight hours) blood glucose levels are typically maintained within a range of between about 70 mg/dL and 110 mg/dL. A diagnosis of, e.g., diabetes can be made if fasting blood glucose levels are elevated beyond a typical range, for example, at levels of about 126 mg/dL or higher. In one embodiment, the present invention provides compounds and methods for maintaining or achieving fasting blood glucose levels at normal blood fasting levels, i.e., within a range of about 70 mg/dL to 110 mg/dL. In another embodiment, the present invention provides compounds and methods for elevating or restoring low fasting blood glucose levels (i.e., blood glucose levels below normal fasting levels) to within a range of about 70 mg/dL to 110 mg/dL. In another embodiment, the present invention provides compounds and methods for decreasing (lowering) or restoring elevated fasting blood glucose levels (i.e., blood glucose levels elevated above normal fasting levels) to below about 126 mg/dL and above 70 mg/dL, more preferably below about 120 mg/dL and above 70 mg/dL, and most preferably below about 110 mg/dL and above 70 mg/dL.

Another measurement of blood glucose levels is a random blood glucose test. Blood glucose levels measured in this fashion typically exhibit values in the low- to mid-100's (mg/dL). A random blood glucose level of about 180 mg/dL or higher is a condition of hyperglycemia, and a level of about 200 mg/dL or higher is indicative of the presence of or a risk for developing a disorder associated with impaired glucose regulation, e.g., diabetes. Therefore, in one aspect, the present invention provides methods and compounds for maintaining or achieving blood glucose levels, determined by random blood glucose test, at normal levels, i.e., low- to mid-100's (mg/dL). In another aspect, the methods and compounds of the present invention can be used to restore blood glucose levels that are decreased below normal levels as determined by random blood glucose test to those normal levels, i,e., low- to mid-100's (mg/dL). In a further aspect, the methods and compounds of the present invention can be used to lower/reduce blood glucose levels elevated above normal levels, i.e., above low- to mid-100's (mg/dL). In various aspects, the methods and compounds reduce elevated blood glucose levels to levels below about 200 mg/dL and above 100 mg/dL, more preferably to levels below about 180 mg/dL and above 100 mg/dL, and most preferably to levels below about 150 mg/dL and above 100 mg/dL.

An oral glucose tolerance test can also be used to identify a subject having or at risk for impaired glucose regulation, hyperglycemia, diabetes, etc. In this test, an individual drinks a sugar-water solution following an overnight fast. Blood glucose levels are then tested over several hours. In a person having normal glucose tolerance/regulation, e.g., an individual without diabetes, etc., measured blood glucose levels will rise after the solution is administered and then fall quickly. A normal blood glucose reading two hours after drinking the sugar-water solution is less than about 140 mg/dL, and all readings taken between zero and two hours are below about 200 mg/dL. Impaired glucose tolerance is generally diagnosed if the blood glucose level measured during an oral glucose tolerance test is in the range of about 140 mg/dL to 199 mg/dL. Diabetes is generally diagnosed if the measured blood glucose level is about 200 mg/dL or higher. Methods and compounds of the present invention are useful to maintain, restore, or achieve normal blood glucose levels following an oral glucose tolerance test.

Expression of Glucose Regulatory Factors

In one embodiment, the invention provides methods and compounds for increasing expression of genes whose products are involved in glucose uptake and utilization by cells. Such genes include, but are not limited to, glucose transporters, such as glucose transporter (GluT)-1 and GluT-3; and glycolytic enzymes such as aldolase-A, enolase-1, hexokinase-1, hexokinase-2, phosphofructokinase-L, and phosphofructokinase-P. Therapeutic upregulation of glucose transport and utilization will effectively reduce insulin resistance, lower blood glucose and, thereby, produce a beneficial effect in patients with metabolic disorders, e.g., Type 2 diabetes, hyperglycemia, impaired glycemic control, impaired glucose tolerance, etc.

In one aspect, the present invention provides compounds and methods for treating or preventing hyperglycemia. Such compounds and methods are suitable for treating or preventing disorders associated with hyperglycemia, such as, for example, elvated blood glucose levels resulting from increased glucose release, decreased glucose utilization, and/or impaired glucose uptake. These disorders are further associated with insulin resistance, impaired glucose tolerance, Type 2 diabetes, and/or obesity.

In one aspect, methods of the present invention provide means for activating a repertoire of gene expression that regulates levels and activity of glucose and glucose metabolism, including processing and utilization, throughout the body. The methods compensate for defects in the body's natural mechanisms for regulating such processes, e.g., due to loss of production or response to insulin. The present invention provides methods of treating metabolic conditions or disorders associated with impaired glycemic control. Such disorders include, but are not limited to, impaired glucose tolerance (IGT) or pre-diabetes, diabetes, hyperglycemia, etc.

The invention specifically contemplates selectively designing prodrug compounds such that they are activated upon uptake by specific organs. For example, as the liver produces many of the proteins involved in fat homeostasis, the invention contemplates selectively targeting the liver in the present methods. Selective upregulation of genes, e.g., aldolase, in the liver can be achieved using compounds that are converted from an inactive to an active form by liver specific enzymes. For example, a carboxylic acid on an active compound can be replaced with a corresponding alcohol. The activity of alcohol dehydrogenase (ADH) in the liver would convert such a compound into active form. As other organs lack ADH activity, the compound would be selectively activated only in the liver. Similarly, compounds used in the method of the invention may be targeted to other organs, e.g., adipose tissue, kidney, skeletal muscle, heart, etc.

Insulin

Insulin is critical in regulating metabolic equilibrium, stimulating glucose uptake in most cells of the body. When insulin is present, most cells use glucose as their metabolic fuel, fat cells use glucose to synthesize fat, and liver cells convert glucose to glycogen and fat. A rise in blood glucose is immediately followed by a rise in blood insulin, its secretion stimulated by several of the events associated with glucose intake. Upon subsequent reduction in blood glucose levels, insulin release diminishes rapidly, and the entry of glucose into cells other than those of the nervous system is inhibited. Without a supply of glucose, cells use glycogen and fat as metabolic fuels. Liver and fat cells begin breaking down stored glycogen and fat. As a result, the liver supplies glucose to the blood rather than taking it from the blood, and both the liver and adipose tissue supply fatty acids to the blood. Therefore, low insulin levels decrease glucose uptake in insulin-sensitive tissues, promote gluconeogenesis and glycogenolysis (glycogen breakdown) in the liver, decrease glycogen synthesis, and promote mobilization of stored glycogen and fat.

Failure of the body to produce insulin, or to respond to insulin, e.g., reduced insulin sensitivity, i.e., insulin resistance, etc., can lead to various disorders, including diabetes and hyperglycemia.

Impaired glucose transport is causally related to insulin resistance. The present invention contemplates methods for reducing insulin resistance in order to restore impaired glucose transport or increase glucose transport. Methods for lowering or reducing insulin resistance are provided by the present invention. In certain aspects, insulin resistance is lowered by stabilizing HIFα. In other aspects, methods are provided for lowering insulin resistance by inhibiting HIF PH activity.

Increased insulin sensitivity is positively correlated with high plasma levels of insulin like growth factor binding protein-1 (IGFBP-1). IGFBP-1 plasma levels are also negatively correlated to body mass index in adolescents. (Travers et al. (1998) J Clin Endocrinol Metab 83:1935-1939.) In addition, low IGFBP-1 levels correlate with increased cardiovascular risk Type 2 diabetes. (Gibson et al. (1996) J Clin Endocrinol Metab 81:860-863.) Therefore, increased levels of IGFBP-1 would be desirable in restoring or maintaining insulin sensitivity, i.e., in treating insulin resistance.

In addition, a genetic defect that affects phosphofructo-1-kinase (PFK) leads to insulin resistance and Type 2 diabetes. Because PFK is the rate-limiting enzyme in the glycolytic cascade, decreased activity of this enzyme in particular and of the glycolytic cascade in general are apparently related to insulin resistance and Type 2 diabetes. Therefore, increased levels of PFK and other glycolytic factors, e.g., aldolase, enolase, hexokinases, etc., would be desirable in restoring or maintaining insulin sensitivity, e.g., decreasing insulin resistance.

The present compounds were shown to increase IGFBP-1, PFK, and other glycolytic enzyme expression. (See, e.g., Example 4.) Therefore, in one embodiment, the invention provides methods and compounds for coordinate expression of genes whose products are involved in glucose processing and utilization, e.g., IGFBP-1, PFK, etc. In another embodiment, the present invention provides methods and compounds for increasing insulin sensitivity, e.g., reducing insulin resistance, etc., by coordinate expression of such genes. In one aspect, the method encompasses, e.g., stabilizing HIFα in a subject. The invention further provides methods for increasing insulin sensitivity in a subject by administering to a subject a compound of the present invention, e.g., an agent that inhibits HIF hydroxylase activity.

Glycated Hemoglobin

Results from the Diabetes Control and Complications Trial (DCCT) have demonstrated that improvement of glycemic control reduces diabetic complications including nonproliferative and proliferative retinopathy (47% reduction), microalbuminuria (39% reduction), clinical nephropathy (54% reduction), and neuropathy (60% reduction). (DCCT Research Group (1993) N Engl J Med 329:977-986.) Additionally, the United Kingdom Prospective Diabetes Study (UKPDS) demonstrated that glycemic control was associated with a reduction in microvascular complications, and strict blood pressure control significantly reduced both macro- and microvascular complications. (UKPDS Group (1998) Lancet 352:837-853.)

Glycated hemoglobin (also known as glycohemoglobin, glycosylated hemoglobin, HbA1c, or HbA1) is formed by the attachment of various sugars (most commonly glucose) to the hemoglobin molecule, and is formed at a rate that is directly proportional to the blood glucose concentration. Measurement of glycated hemoglobin levels provides an accurate index of the mean blood glucose concentration over the preceding 2 to 3 months. Clinically, glycated hemoglobin levels provide an assessment of glycemic control in diabetic patients. Normal (non-diabetic) glycated hemoglobin levels are in the range of 4 to 6%. In the study of diabetic individuals, the DCCT found that lowering or maintaining HbA1c levels to an average HbA1c level of 7.2% resulted in a 76% reduction in retinopathy, a 60% reduction in neuropathy, a 50% reduction in kidney disease, and a 35% reduction in cardiovascular disease compared to diabetic individuals with higher HbA1c levels.

The present invention provides compounds and methods for decreasing glycated hemoglobin levels. In one embodiment, methods and compounds of the present invention are useful to maintain, restore, or achieve glycated hemoglobin levels at about 4 to 6%. In another embodiment, methods and compounds of the present invention reduce glycated hemoglobin levels to below about 9%, more preferably below about 8%, and most preferably, below about 7%.

Diabetes and Obesity

Obesity is a risk factor for, and sometimes an exacerbating side effect of diabetes. Obesity is characterized by excess fat deposition and, in particular, by elevated levels of visceral or central fat. Therefore, treatment or prevention of obesity can minimize the risk for or development of diabetes, and, in fact, weight reduction regimes are often prescribed for diabetic individuals or individuals diagnosed as at risk for diabetes.

Compounds of the invention have been shown to prevent or retard weight gain and to reduce visceral and abdominal fat in in vivo studies. (See, e.g., Examples 9 and 10) Therefore, in one aspect, the invention provide methods for treating or preventing diabetes by reducing or preventing obesity. In one aspect, the method encompasses, e.g., stabilizing HIFα in a subject. The invention further provides methods for treating or preventing obesity in a subject by administering to a subject a compound of the present invention, e.g., an agent that inhibits HIF hydroxylase activity.

As stated above, diabetes is associated with various disorders and diseases. For example, cardiovascular disease (CVD) is a leading cause of death in Type 2 diabetic patients. Individuals with Type 2 diabetes are two to six times more likely to die from CVD than non-diabetic individuals. A significant number of deaths in these patients are attributed to chronic heart disease (CHD). Hyperlipidemia is common in Type 2 diabetes and contributes to the incidence of CHD. A common lipid profile of Type 2 diabetic individuals includes higher total triglycerides and lower HDL cholesterol than non-diabetic individuals. Similar abnormalities in triglyceride and HDL cholesterol are observed in non-diabetic individuals that are obese (in particular individuals with increased visceral fat), hypertensive, and insulin resistant (e.g., metabolic syndrome). Increased triglyceride levels have been implicated as a risk factor for cardiovascular disease and elevated triglycerides are an important component of the metabolic syndrome. Prevention or treatment of diabetic dyslipidemia may decrease the risk for developing macrovascular complications.

Diabetes and Hypertension

Hypertension, or elevated or high blood pressure, is a risk factor for diabetes. In addition, high blood pressure and associated ill effects can develop in association with or as a result of diabetes. Therefore, treatment or prevention of hypertension can minimize the risk for or development of diabetes, and a therapeutic approach that addressed this aspect of diabetes would be valuable.

The present invention provides such an approach. In particular, the methods and compounds of the present invention can be applied to treat hypertension associated with diabetes. For example, compounds of the present invention increased expression of blood pressure regulatory factors such as, e.g., adrenomedullin and nitric oxide synthase. (See, e.g., Example 12.) Therefore, in one aspect, the invention provides methods for treating or preventing diabetes by reducing or preventing hypertension. In one aspect, the method encompasses, e.g., stabilizing HIFα in a subject. The invention further provides methods for treating or preventing hypertension in a subject by administering to a subject a compound of the present invention, e.g., an agent that inhibits HIF hydroxylase activity.

Coordinated Therapeutic Approach

Diabetes is associated with various deleterious conditions and effects that can occur or develop in parallel, overlapping, and/or successive fashion. For example, hypertension, vascular and circulatory impairment, and obesity can lead to increased risk for—or can develop in association with—diabetes. Therefore, a therapeutic approach that can simultaneously address such a range of risk factors and symptoms would be valuable.

The present invention provides such an approach. In particular, the methods and compounds of the present invention can be applied to achieve multiple effects. For example, as noted above, obesity is a risk factor for development of diabetes. In addition, obesity can develop as a result of diabetes, for example, due to specific therapeutic approaches. Insulin therapy, for example, can lead to increased fat stores and obesity. In particular, insulin mediates uptake of lipids into adipose tissue, increasing obesity, and, in turn, exacerbating insulin resistance. The present invention thus provides, in one aspect, methods for treating or preventing diabetes by treating or preventing obesity and increasing insulin sensitivity in coordinated fashion.

The compounds of the present invention decrease blood glucose levels (see, e.g., Example 6); reduce visceral or abdominal fat (see, e.g., Example 9); increases expression of glycolytic enzymes, thus increasing insulin sensitivity (see, e.g., Example 4); and increases expression of blood pressure regulatory factors (see, e.g., Example 12), thus enabling the body to regulate vascular tone, maintaining normal blood pressure levels or counteracting alterations in vascular tone, e.g., hypertensive effects, etc. Therefore, in one aspect, the present invention provides a method for treatment or prevention of diabetes, the method comprising reducing blood glucose levels and reducing visceral fat by stabilizing HIFα in a subject. Another method further comprises treating or preventing diabetes in a subject by additionally increasing insulin sensitivity. Another method further comprises treating or preventing diabetes in a subject by additionally increasing expression of blood pressure regulatory factors.

Metabolic Disorders

The present invention provides compounds that regulate metabolic activity and methods of using the compounds to treat disorders or conditions associated with metabolic dysfunction. Such disorders include, but are not limited to, diabetes, hyperglycemia, and obesity.

In one aspect, the present invention provides methods of using the compounds to prevent or treat diabetes, the method comprising administering a therapeutically effective amount of the compound or a pharmaceutically acceptable salt thereof either alone or in combination with a pharmaceutically acceptable excipient to a patient in need. In one embodiment, the compound can be administered based on pre-disposing conditions, e.g., impaired glucose homeostasis, impaired glucose tolerance, hyperglycemia, diabetes, or obesity.

In another aspect, the present invention provides methods of using the compounds to treat hyperglycemia, the method comprising administering a therapeutically effective amount of the compound or a pharmaceutically acceptable salt thereof either alone or in combination with a pharmaceutically acceptable excipient to a patient in need. In one embodiment, the compound is administered to a patient diagnosed with a condition associated with the development of hyperglycemia, e.g., diabetes.

The compounds can be administered in combination with various other therapeutic approaches. In one embodiment, the compound is administered in combination with exogenous insulin, e.g., human recombinant insulin.

Glucose Regulation

Methods and compounds of the present invention increased aldolase expression. These results demonstrated that methods and compounds of the present invention are useful for regulating expression of genes involved in glycolysis. Methods and compounds for regulating glucose metabolism, e.g., by increasing glycolysis are provided.

Methods and compounds for increasing expression of GluT-1 are provided by the present invention. In one aspect, the methods of the invention regulate expression of factors involved in glucose uptake. Thus methods and compounds of the present invention provide a therapeutic approach for increasing glucose transport into cells. Therapeutic upregulation of glucose transport factors will effectively reduce insulin resistance, increase insulin sensitivity, reduce blood glucose levels, and, thereby, produce a beneficial effect in patients with hyperglycemia or diabetes.

Methods and compounds of the present invention increased expression of glucose regulatory factors including phosphofructokinase-P, phosphofructokinase-L, enolase-1, GluT-1, lactate dehydrogenase, aldolase-1, and hexokinase-1 in kidney, liver, and lung. In one embodiment, the methods of the invention coordinately regulate expression of genes whose products are involved in glucose uptake and utilization, thereby regulating glucose metabolism. Therapeutic upregulation of glucose transport and utilization will reduce insulin resistance, increase insulin sensitivity, and reduce blood glucose levels, thereby providing means for treating hyperglycemia and diabetes.

Expression of the gene encoding insulin like growth factor binding protein-1 (IGFBP-1) is increased in kidney and liver using methods and compounds of the present invention. High plasma levels of IGFBP-1 have been positively correlated with increased insulin sensitivity. Therefore, methods and compounds of the present invention are useful for increasing insulin sensitivity and providing enhanced glucose transport, thereby regulating glucose metabolism. Therapeutic increase in insulin sensitivity and glucose transport will reduce blood glucose levels, thereby providing means for treating hyperglycemia and diabetes.

The present invention provides methods and compounds for increasing glucose uptake in cells. Compounds and methods of the present invention increase glucose uptake in the presence of insulin, indicating that compounds and methods of the invention increase insulin sensitivity of cells, resulting in increased glucose uptake and altered glucose regulation. Therapeutic increases in insulin sensitivity and glucose uptake are useful for treating individuals with decreased insulin sensitivity or with insulin resistance, thereby reducing blood glucose levels and providing means for treating hyperglycemia and diabetes.

Methods and compounds of the present invention are also useful for increasing insulin-stimulated glucose uptake in tissues. Methods and compounds of the invention can be used to increase glucose uptake in tissues, increasing sensitivity to insulin. Increased glucose uptake provides means for reducing blood glucose levels in individuals with elevated glucose levels, such as in hyperglycemia or diabetes, or in individuals with deficiencies in achieving or maintaining glucose homeostasis. Therefore, methods and compounds of the present invention are useful for treating hyperglycemia and diabetes by increasing insulin sensitivity, increasing glucose uptake, and reducing blood glucose levels.

Animals treated with compounds of the present invention showed a dose-dependent decrease in blood glucose levels. Blood glucose levels were maintained at desirable levels by altering compound dose. Therefore, in one aspect, compounds and methods of the present invention are useful for regulating blood glucose levels. In another aspect, compounds and methods of the present invention are useful for decreasing blood glucose levels. Therefore, method and compounds of the invention are useful to therapeutically decrease blood glucose levels. By decreasing blood glucose levels, the present invention provides means for treating hyperglycemia and diabetes.

Administration of compounds of the present invention improved glucose clearance from circulation in an animal model of diet-induced obesity and impaired glucose tolerance. Increased glucose clearance reduces blood glucose levels. Therefore, in one aspect, the present methods are useful for regulating glucose metabolism by increasing glucose clearance or reducing blood glucose levels in individuals with impaired glucose tolerance, such as, for example, in obese individuals. In another aspect, methods and compounds of the present invention restore or maintain glucose homeostasis in individuals with impaired glucose tolerance. Therapeutic increase in glucose clearance and reduction in blood glucose levels are useful for treating patients, including patients with diabetes or at risk for developing diabetes.

Treatment of Diabetes

Methods and compounds of the present invention decreased blood glucose levels in an animal model of diabetes. Additionally, methods and compounds of the invention restored and achieved glucose homeostasis in an animal model of diabetes and impaired glucose tolerance. Reduced blood glucose levels by administration of compounds of the present invention suggest that compounds of the invention are useful to therapeutically decrease blood glucose levels in individuals with hyperglycemia or diabetes. Compounds and methods of the invention are useful for restoring, achieving, or maintaining glucose homeostasis by regulating glucose metabolism.

Treatment of animals with compounds of the invention reduced the accumulation of glycated hemoglobin in an animal model of diabetes. Glycated hemoglobin levels reflect glycemic control and maintenance of glucose homeostasis in diabetic patients or in individuals with hyperglycemia. Reduced levels of glycated hemoglobin indicate that compounds and methods of the invention are useful to alter glucose regulation in individuals, thereby restoring, achieving, or maintaining glucose homeostasis. Therefore, compounds and methods of the present invention are useful for treating hyperglycemia and diabetes by regulating glucose metabolism and restoring, achieving, or maintaining glucose homeostasis.

Animals treated with compounds of the present invention showed a dose-dependent retardation in weight gain. In particular, a dose-dependent reduction in visceral fat pads was observed in animals treated with compound. Therefore, compounds and methods of the present invention are useful for reducing fat stores and decreasing visceral fat. Obesity, in particular obesity associated with excess visceral, abdominal, or central fat, is associated with development of hyperglycemia and diabetes. In particular, obesity is associated with decreased insulin sensitivity, increased insulin resistance, etc., which lead to hyperglycemia and development of diabetes. In one aspect, methods and compounds of the present invention reduce the risk of developing hyperglycemia or diabetes by reducing visceral fat. In another aspect, methods and compounds of the invention reduce the risk of developing hyperglycemia or diabetes by reducing obesity.

Pharmaceutical Formulations and Routes of Administration

The compositions of the present invention can be delivered directly or in pharmaceutical compositions containing excipients, as is well known in the art. Present methods of treatment can comprise administration of an effective amount of a compound of the present invention to a subject having or at risk for a metabolic disorder; particularly a disorder associated with glucose regulation, e.g., diabetes, hyperglycemia, etc. In a preferred embodiment, the subject is a mammalian subject, and in a most preferred embodiment, the subject is a human subject.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, ed. (2000) Remington's Pharmaceutical Sciences, supra; and Hardman, Limbird, and Gilman, eds. (2001) The Pharmacological Basis of Therapeutics, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP, FDA web page (www.fda.gov), Inactive Ingredient Guide 1996, and Handbook of Pharmaceutical Additives, ed. Ash; Synapse Information Resources, Inc. 2002.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid or a liquid formulation, for example a gel, a (micro-) emulsion, an ointment, a solution, a (nano/micro-) suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons dervided from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

For composition useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a compound, agent, or drug of the present invention refers to an amount or dose of the compound, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal, or human that is being sought by the researcher, veterinarian, medical doctor, or other clinician, e.g., regulation of glucose metabolism, decrease in elevated or increased blood glucose levels, treatment or prevention of a disorder associated with altered glucose metabolism, e.g., diabetes, etc Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, e.g., regulation of glucose metabolism, decrease in blood glucose levels, etc., i.e., minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Compounds and Screening Methods Therefor

A compound of the invention is a compound that inhibits hydroxylase activity, specifically wherein the hydroxylase activity is the activity of a 2-oxoglutarate dioxygenase enzyme. More preferably, the hydroxylase activity is the activity of a HIF hydroxylase enzyme. Most preferably, the hydroxylase activity is the activity of a HIF prolyl hydroxylase enzyme A method of the invention is a method that relies on the stabilization of HIFα to achieve a particular result in a subject. Preferably, the methods of the present invention are accomplished through administration of a compound to stabilize HIFα and achieve a particular result in that subject. Most preferably, the methods are accomplished by administration of a compound of the invention.

The compounds of the present invention are exemplary for use in the present methods, which relate to stabilization of HIFα. In particular, the present invention provides compounds, and methods for screening for and identifying additional compounds that inhibit HIF hydroxylase activity and/or HIFα hydroxylation, stabilize HIFα, etc. Compounds of the invention include compounds that inhibit hydroxylase activity, preferably wherein the hydroxylase activity is the activity of a 2-oxoglutarate dioxygenase enzyme, and more preferably wherein the hydroxylase activity is the activity of a HIF hydroxylase. The HIF hydroxylase may hydroxylate any amino acid, including, e.g., a proline or asparagine residue, etc., in a HIF protein, preferably in a HIFα subunit. In an especially preferred embodiment, the hydroxylase activity is the activity of a HIF prolyl hydroxylase and/or a HIF asparaginyl hydroxylase.

Inhibitors of 2-oxoglutarate dioxygenase activity are known in the art. For example, several small molecule inhibitors of procollagen prolyl 4-hydroxylase have been identified. (See, e.g., Majamaa et al. (1984) Eur J Biochem 138:239-245; Majamaa et al. (1985) Biochem J 229:127-133; Kivirikko and Myllyharju (1998) Matrix Biol 16:357-368; Bickel et al. (1998) Hepatology 28:404-411; Friedman et al. (2000) Proc Natl Acad Sci USA 97:4736-4741; and Franklin et al. (2001) Biochem J 353:333-338; all incorporated by reference herein in their entirety.) Small molecule inhibitors of HIF hydroxylases have also been identified. (See, e.g., International Publication Nos. WO 02/074981, WO 03/049686, and WO 03/080566, all incorporated herein by reference in their entirety.) The present invention specifically contemplates the use of these and other compounds that can be identified using methods known in the art.

All of the enzymes in the 2-oxoglutarate dioxygenase family require oxygen, $Fe^{2+}$, 2-oxoglutarate, and ascorbic acid for their hydroxylase activity. (See, e.g., Majamaa et al. (1985) Biochem J 229:127-133; Myllyharju and Kivirikko (1997) EMBO J 16:1173-1180; Thornburg et al. (1993) 32:14023-14033; and Jia et al. (1994) Proc Natl Acad Sci USA 91:7227-7231.) Therefore, compounds of the invention include, but are not limited to, iron chelators, 2-oxoglutarate mimetics, and modified amino acid, e.g., proline or asparagine, analogs.

In particular embodiments, the present invention provides for use of structural mimetics of 2-oxoglutarate. Such compounds may inhibit the target 2-oxoglutarate dioxygenase enzyme competitively with respect to 2-oxoglutarate and noncompetitively with respect to iron. (Majamaa et al. (1984) supra; and Majamaa et al. (1985) supra.) Specifically contemplated are compounds described, e.g., in Majamaa et al., supra; Kivirikko and Myllyharju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19:812-815; Franklin et al. (2001) Biochem J 353:333-338; and International Publication No. WO 03/049686, all incorporated by reference herein in their entirety.

Exemplary compounds include phenanthrolines including, but not limited to, those described in U.S. Pat. Nos. 5,916,898 and 6,200,974, and International Publication No. WO 99/21860; heterocyclic carbonyl glycines including, but not limited to, substituted quinoline-2-carboxamides and esters thereof as described, e.g., in U.S. Pat. Nos. 5,719,164 and 5,726,305; substituted isoquinoline-3-carboxamides and esters thereof as described, e.g., in U.S. Pat. No. 6,093,730; 3-methoxy pyridine carbonyl glycines and esters thereof as described, e.g., in European Patent No. EP 0 650 961 and U.S. Pat. No. 5,658,933; 3-hydroxypyridine carbonyl glycines and esters thereof as described, e.g., in U.S. Pat. Nos. 5,620,995 and 6,020,350; 5-sulfonamidocarbonyl pyridine carboxylates and esters thereof as described, e.g., in U.S. Pat. Nos. 5,607,954, 5,610,172, and 5,620,996. All compounds listed in these patents, in particular, those compounds listed in the compound claims and the final products of the working examples, are hereby incorporated into the present application by reference herein.

Therefore, preferred compounds of the present invention include, e.g., heterocyclic carboxamides. Specifically preferred heterocyclic carboxamides include, e.g., isoquinolines, quinolines, pyridines, cinnolines, carbolines, etc. Additionally, structural classes of preferred compounds include anthraquinones, azafluorenes, azaphenanthrolines, benzimidazoles, benzofurans, benzopyrans, benzothiophenes, catechols, chromanones, α-diketones, furans, N-hydroxyamides, N-hydroxyureas, imidazoles, indazoles, indoles, isothiadiazoles, isothiazoles, isoxadiazoles, isoxazoles, α-keto acids, α-keto amides, α-keto esters, α-keto imines, oxadiazoles, oxalyl amides, oxazoles, oxazolines, purines, pyrans, ppyrazines, pyrazoles, pyrazolines, pyridazines, pyridines, quinazolines, phenanthrolines, tetrazoles, thiadiazoles, thiazoles, thiazolines, thiophenes, and triazoles.

The following exemplary compounds are used in the present examples to demonstrate the methods of the invention described herein: [(7-Chloro-3-hydroxy-quinoline-2-carbonyl)-amino]-acetic acid (compound A), [(1-Chloro4-hydroxy-isoquinoline-3-carbonyl)-amino]-acetic acid (compound B), [(4-Hydroxy-7-phenoxy-isoquinoline-3-carbonyl)-amino]-acetic acid (compound C), 4-Oxo-1,4-dihydro-[1,10]phenanthroline-3-carboxylic acid (compound D), [(1-Chloro-4-hydroxy-7-methoxy-isoquinoline-3-carbonyl)-amino]-acetic acid (compound E), [(3-Hydroxy-6-isopropoxy-quinoline-2-carbonyl)-amino]-acetic acid (compound F), [(3-Hydroxy-pyridine-2-carbonyl)-amino]-acetic acid (compound G), and [(7-Benzyloxy-1-chloro-4-hydroxy-isoquinoline-3-carbonyl)-amino]-acetic acid methyl ester (compound H).

Various assays and screening techniques, including those described below, can be used to identify compounds of the present invention, i.e., compounds that inhibit hydroxylase activity. These compounds are suitable for use in the present methods. Additional compounds suitable for use in the present methods, i.e., compounds that stabilize HIFα, can be identified by one of skill in the art using available assay and screening methodology.

Assays will typically provide for detectable signals associated with the consumption of a reaction substrate or production of a reaction product. Detection can involve, for example, fluorophores, radioactive isotopes, enzyme conjugates, and other detectable labels well known in the art. The results may be qualitative or quantitative. Isolation of the reaction product may be facilitated by a label, such as biotin or a histidine tag that allows purification from other reaction components via precipitation or affinity chromatography.

Assays for hydroxylase activity are standard in the art. Such assays can directly or indirectly measure hydroxylase activity. For example, an assay can measure hydroxylated residues, e.g., proline, asparagine, etc., present in the enzyme substrate, e.g., a target protein, a synthetic peptide mimetic, or a fragment thereof. (See, e.g., Palmerini et al. (1985) J Chromatogr 339:285-292.) A reduction in hydroxylated proline or asparagine in the presence of a compound is indicative of a compound that inhibits hdroxylase activity. Alternatively, assays can measure other products of the hydroxylation reaction, e.g., formation of succinate from 2-oxoglutarate. (See, e.g., Cunliffe et al. (1986) Biochem J 240:617-619.) Kaule and Gunzler (1990; Anal Biochem 184:291-297) describe an exemplary procedure that measures production of succinate from 2-oxoglutarate.

Procedures such as those described above can be used to identify compounds that modulate HIF hydroxylase activity. An exemplary procedure is described in Example 14 (infra). Target protein may include HIFα or a fragment thereof, e.g., HIF(556-575); for example, an exemplary substrate for use in the assay described in Example 14 is DLDLEMLAPYIPM-DDDFQL (SEQ ID NO:5). Enzyme may include, e.g., HIF prolyl hydroxylase (see, e.g., GenBank Accession No. AAG33965, etc.) or HIF asparaginyl hydroxylase (see, e.g., GenBank Accession No. AAL27308, etc.), obtained from any source. Enzyme may also be present in a crude cell lysate or in a partially purified form. For example, procedures that measure HIF hydroxylase activity or indirectly are described in Ivan et al. (2001, Science 292:464468; and 2002, Proc Natl Acad Sci USA 99:13459-13464) and Hirsila et al. (2003, J Biol Chem 278:30772-30780); additional methods are described in International Publication No. WO 03/049686. Measuring and comparing enzyme activity in the absence and presence of the compound will identify compounds that inhibit hydroxylation of HIFα.

Assays for HIFα stabilization and/or HIF activation may involve direct measurement of HIFα in a sample (see, e.g., Example 14, infra), indirect measurement of HIFα, e.g., by measuring a decrease in HIFα associated with the von Hippel Lindau protein (see, e.g., International Publication No. WO 00/69908), or activation of HIF responsive target genes or reporter constructs (see, e.g., U.S. Pat. No. 5,942,434). Measuring and comparing levels of HIF and/or HIF-responsive target proteins in the absence and presence of the compound will identify compounds that stabilize HIFα and/or activate HIF.

Compounds that modulate HIF-specific prolyl hydroxylase activity can be identified using an assay based on the hydroxylation-coupled decarboxylation of 2-oxo[1-$^{14}$C]glutarate. (See Hirsila et al (2003) J. Biol. Chem. 278:30772-30780.) The reaction is performed in a 1.0 ml reaction volume containing 10-100 μL of detergent, e.g., Triton-X-100, solubilized cell extract obtained from cells expressing either endogenous HIF prolyl hydroxylase or a recombinant HIF prolyl hydroxylase; 0.05 μmol substrate peptide, e.g., DLD-LEMLAPYIPMDDDFQL (SEQ ID NO: 5); 0.005 μmol of FeSO$_4$, 0.16 μmol of 2-oxo[1-$^{14}$C]glutarate, 2 μmol of ascorbate, 60 μg of catalase, 0.1 μmol dithiothreitol, and 50 μmol Tris-HCl buffer, adjusted to pH 7.8 at 25° C. The enzyme reaction is carried out at 37° C. for 20 minutes. The $^{14}$CO$_2$ produced by the reaction is captured on base-impregnated filter paper suspended in the atmosphere over the reaction mixture and counted in a scintillation counter.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

Example 1

Test Materials

In general, compounds representing prolyl hydroxylase inhibitors used in the methods of the invention were synthesized by standard chemical methods known to those of skill in the art. Compounds were analyzed for purity by high pressure liquid chromatography and stored at room temperature protected from light. During formulation for various uses, compounds were micronized in suspension at 750 rpm for 20 minutes using a PULVERISETTE 7 planetary micro mill (Fritsch GMBH, Germany) to facilitate uniform particle size.

Suspensions of micronized compound for oral gavage were prepared immediately before use. Compound was suspended in aqueous solution containing 0.5% sodium carboxymethyl-cellulose (CMC; Spectrum Chemical, Gardena Calif.), 0.1% polysorbate 80 (Mallinckrodt Baker, Inc., Phillipsburg N.J.) and stirred constantly using a magnetic stirrer or rotary shaker during dose administration. The concentration of the suspensions was calculated to achieve the intended dose level in a given volume. In alternative procedures, compound was weighed and placed in appropriately sized gelatin capsules for oral administration, wherein control animals received empty capsules of the same size; or compound was dissolved in a 100 mM histidine (Mallinckrodt Baker) solution and provided ad libitum in place of water.

For administration by injection, compound was initially mixed with an equimolar amount of sodium hydroxide, in either an aqueous solution of 10% glucose (Spectrum) or 25 mM histidine combined with sodium chloride at isotonicity (Mallinckrodt Baker).

Example 2

Increased in vitro Expression of Glucose Regulatory Factors

The effect of compounds of the present invention on expression of proteins and genes involved in glucose regulation and metabolism as follows. Human 293A cells (adenovirus-transformed fetal kidney epithelium) were plated confluent in 35 mm culture dishes and cultured for 1 day at 37° C., 10% CO$_2$ in DMEM containing 5% FBS and 1% penicillin-streptomycin. The media was changed to Opti-Mem I and incubation was continued for an additional 18 to 24 hours. Vehicle control or compound B was then added to the media and cells were incubated for an additional 24, 48 or 72 hours. Plates were placed on ice, culture supernatant was removed, and lysis buffer-1 (LB-1: 10 mM Tris pH 7.4, 1 mM EDTA, 150 mM sodium chloride, 0.5% IGEPAL) was added. Cell lysates were harvested by scraping, incubated for 15 minutes on ice, and then fractionated by centrifugation at 3000×g for 5 minutes at 4° C. The supernatant, which represented the cytosolic fraction, was collected and cytosolic proteins were separated under reducing conditions using SDS-polyacrylamide gel electrophoresis (SDS-PAGE) with equal amounts of protein loaded per lane.

SDS-PAGE was conducted at 150 V for 2 hours, after which the proteins were transferred to a PVDF membrane at 400 mA for 1.5 hours at 4° C. The membrane was incubated in blocking buffer for 2 hours or overnight and washed once with T-TBS prior to addition of anti-aldolase antibody diluted to working concentration in blocking buffer. After overnight incubation with gentle agitation at 4° C., membranes were washed 4 times with T-TBS, followed by incubation for one hour at room temperature with conjugated secondary antibody diluted in blocking buffer. The membrane was then washed four times with T-TBS prior to development and visualization using X-ray-film and ECL SUPERSIGNAL WEST FEMTO or PICO chemiluminescent substrate (Pierce Chemical Co., Rockford Ill.) according to the manufacturer's instructions.

As seen in FIG. 1A, aldolase expression increased over time in cells treated with compound B for 24, 48, and 72 hours, whereas cultures treated with vehicle control showed no increase in aldolase expression. Compound B-treated cultures displayed no increases in β-tubulin expression, indicating that the increase in aldolase was specific and not associated with a generalized increase in protein expression.

These results indicated that compounds and methods of the invention are useful for regulating expression of genes involved in glycolysis, and suggested that treatment with compound of the present invention increased glucose utilization and metabolism by enhancing glycolysis.

Example 3

Increased in vitro Expression of Glucose Transporter (GluT)-1

Human SSC-25 (squamous cell carcinoma) or rat H9c2 (ventricular cardiomyocyte) cells were grown to confluence in 100 mm culture dishes at 37° C., 10% $CO_2$ in DMEM with 10% fetal calf serum. Cells were then washed twice with PBS and incubated with vehicle control, compound D (10 and 25 µM), or compound C (5, 10, and 20 µM) for 16 hours. Plates were placed on ice, culture supernatant was removed, and lysis buffer-1 (LB-1: 10 mM Tris pH 7.4, 1 mM EDTA, 150 mM sodium chloride, 0.5% IGEPAL) was added. Cell lysates were harvested by scraping, incubated for 15 minutes on ice, and then centrifuged at 3000×g for 5 minutes at 4° C. The supernatant, which represents the cytosolic fraction, was collected and cytosolic proteins were separated under reducing conditions using SDS-polyacrylamide gel electrophoresis (SDS-PAGE) with equal amounts of protein loaded per lane.

SDS-PAGE was conducted at 150 V for 2 hours, after which the proteins were transferred to a PVDF membrane at 400 mA for 1.5 hours at 4° C. The membrane was incubated in blocking buffer for 2 hours or overnight and washed once with T-TBS prior to addition of anti-GluT-1 antibody (Alpha Diagnostics) diluted to working concentration in blocking buffer. After overnight incubation with gentle agitation at 4° C., membranes were washed 4 times with T-TBS, followed by incubation for one hour at room temperature with conjugated secondary antibody diluted in blocking buffer. The membrane was then washed four times with T-TBS prior to development and visualization using X-ray-film and ECL SUPERSIGNAL WEST PICO chemiluminescent substrate (Pierce Chemical Co., Rockford Ill.) according to the manufacturer's instructions.

The data shown in FIG. 1B indicate that both compound D and compound C increased protein levels of GluT-1, a major inducible glucose transporter mediating glucose uptake, in SCC-25 and H9c2 cells, respectively. The ability of compounds and methods of the invention to increase GluT-1 expression in cells provides a means for examining the effect of compounds on glucose uptake in vitro. These results showed that compounds and methods of the present invention are useful for increasing expression of proteins involved in glucose uptake, and thus provide a therapeutic approach to enhance glucose uptake and lower blood glucose levels, particularly in patients with hyperglycemia, diabetes, or other deficiencies in regulating glucose homeostasis.

Example 4

Increased in vivo Expression of Glucose Regulatory Factors

To determine gene induction patterns over time, twenty four Swiss Webster male mice (30-32 g) were obtained from Simonsen, Inc. and treated by oral gavage with a 4 ml/kg volume of either 0.5% carboxymethyl cellulose (CMC; Sigma-Aldrich, St. Louis Mo.) (0 mg/kg/day) or 1.25% compound B (25 mg/ml in 0.5% CMC) (100 mg/kg). At 4, 8, 16, 24, 48, or 72 hours after the final dose, animals were anesthetized with isoflurane. The mice were then sacrificed and tissue samples of kidney, liver, brain, lung, and heart were isolated and stored in RNALATER solution (Ambion) at −80° C.

To investigate the dose response of compounds of the present invention, twelve Swiss Webster male mice (30-32 g) (obtained from Simonsen, Inc., Gilroy Calif.) were treated by oral gavage once per day for 4 days with a 4 ml/kg volume of either 0.5% carboxymethyl cellulose (CMC; Sigma-Aldrich, St. Louis Mo.), compound D (25 mg/ml in 0.5% CMC) (100 mg/kg/day), or compound B (7.5 and 25 mg/ml in 0.5% CMC) (30 and 100 mg/kg/day, respectively). Four hours after the final dose, animals were anesthetized, sacrificed, and approximately 150 mg of liver and each kidney were isolated and stored in RNALATER solution (Ambion) at −20° C.

RNA from tissues obtained from the experiments described above was isolated using the following protocol. A 50 mg section of each organ was diced, 875 µl of RLT buffer (RNEASY kit; Qiagen Inc., Valencia Calif.) was added, and the pieces were homogenized for about 20 seconds using a rotor-stator POLYTRON homogenizer (Kinematica, Inc., Cincinnati Ohio). The homogenate was micro-centrifuged for 3 minutes to pellet insoluble material, the supernatant was transferred to a new tube and RNA was isolated using an RNEASY kit (Qiagen) according to the manufacturer's instructions. The RNA was eluted into 80 µL of water and quantitated with RIBOGREEN reagent (Molecular Probes, Eugene Oreg.). Genomic DNA was then removed from the RNA using a DNA-FREE kit (Ambion Inc., Austin Tex.) according to the manufacturer's instructions. The absorbance at 260 and 280 nm was measured to determine RNA purity and concentration.

Alternatively, tissue samples were diced and homogenized in TRIZOL reagent (Invitrogen Life Technologies, Carlsbad Calif.) using a rotor-stator POLYTRON homogenizer (Kinematica). Homogenates were brought to room temperature, 0.2 volumes chloroform was added, and samples were mixed vigorously. Mixtures were incubated at room temperature for several minutes and then were centrifuged at 12,000 g for 15 min at 4° C. The aqueous phase was collected and 0.5 volumes of isopropanol were added. Samples were mixed, incubated at room temperature for 10 minutes, and centrifuged for 10 min at 12,000 g at 4° C. The supernatant was removed and the pellet was washed with 75% EtOH and centrifuged at 7,500 g for 5 min at 4° C. Genomic DNA was then removed from the RNA using a DNA-FREE kit (Ambion Inc., Austin Tex.) according to the manufacturer's instructions. The absorbance at 260 and 280 nm was measured to determine RNA purity and concentration.

RNA was precipitated in 0.3 M sodium acetate (pH 5.2), 50 ng/ml glycogen, and 2.5 volumes of ethanol for one hour at −20° C. Samples were centrifuged and pellets were washed with cold 80% ethanol, dried, and resuspended in water. Double stranded cDNA was synthesized using a T7-(dT)24 first strand primer (Affymetrix, Inc., Santa Clara Calif.) and the SUPERSCRIPT CHOICE system (Invitrogen) according to the manufacturer's instructions. The final cDNA was extracted with an equal volume of 25:24:1 phenol:chloroform:isoamyl alcohol using a PHASE LOCK GEL insert (Brinkman, Inc., Westbury N.Y.). The aqueous phase was collected and cDNA was precipitated using 0.5 volumes of 7.5 M ammonium acetate and 2.5 volumes of ethanol. Alternatively, cDNA was purified using the GENECHIP sample cleanup module (Affymetrix) according to the manufacturer's instructions.

Biotin-labeled cRNA was synthesized from the cDNA in an in vitro translation (IVT) reaction using a BIOARRAY HIGHYIELD RNA transcript labeling kit (Enzo Diagnostics, Inc., Farmingdale N.Y.) according to the manufacturer's instructions. Final labeled product was purified and fragmented using the GENECHIP sample cleanup module (Affymetrix) according to the manufacturer's instructions.

Hybridization cocktail was prepared by bringing 5 µg probe to 100 µl in 1× hybridization buffer (100 mM MES, 1 M

[Na⁺], 20 mM EDTA, 0.01% Tween 20), 100 µ/ml herring sperm DNA, 500 µg/ml acetylated BSA, 0.03 nM contol oligo B2 (Affymetrix), and 1× GENECHIP eukaryotic hybridization control (Affymetrix). The cocktail was sequentially incubated at 99° C. for 5 minutes and 45° C. for 5 minutes, and then centrifuged for 5 minutes. The Murine genome U74AV2 array (MG-U74Av2; Affymetrix) was brought to room temperature and then pre-hybridized with 1× hybridization buffer at 45° C. for 10 minutes with rotation. The buffer was then replaced with 80 µl hybridization cocktail and the array was hybridized for 16 hours at 45° C. at 60 rpm with counter balance. Following hybridization, arrays were washed once with 6× SSPE, 0.1% Tween 20, and then washed and stained using R-phycoerythrin-conjugated streptavidin (Molecular Probes, Eugene Oreg.), biotinylated goat anti-streptavidin antibody (Vector Laboratories, Burlingame Calif.), and a GENECHIP Fluidics Station 400 instrument (Affymetrix) according to the manufacturer's micro_1v1 protocol (Affymetrix). Arrays were analyzed using a GENEARRAY scanner (Affymetrix) and Microarray Suite software (Affymetrix).

The Murine Genome U74AV2 array (Affymetrix) represents all sequences (~6,000) in Mouse UniGene database build 74 (National Center for Biotechnology Information, Bethesda Md.) that have been functionally characterized and approximately 6,000 unannotated expressed sequence tag (EST) clusters.

Figure 2:
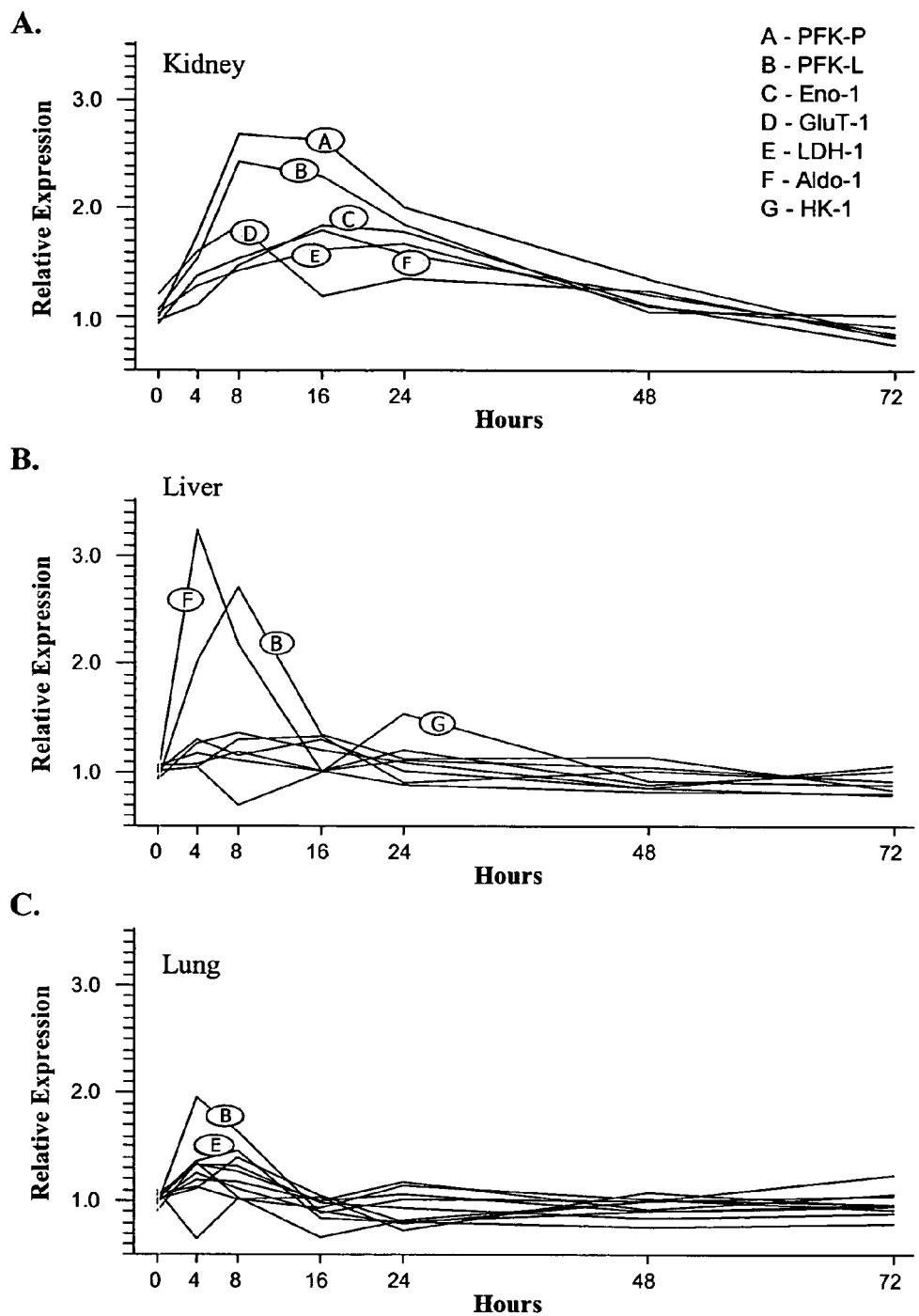
FIGS. 2A, 2B, and 2C show increase in expression of genes involved in glucose regulation in the kidney, liver, and lung, respectively, in animals treated with a compound of the invention.

As shown in FIGS. 2A, 2B, and 2C, expression of genes encoding enzymes involved in glucose regulation was increased in a coordinated fashion after treatment with compound B. Transcript patterns represented in FIGS. 2A, 2B, and 2C include platelet-type phosphofructokinase (PFK)-P (A), liver-type PFK-L (B), enolase-1 (C), glucose transporters (GluT)-1 (D), lactate dehydrogenase-1 (E), aldolase-1 (F), and hexokinase-1 (G). In the time course, most mRNA levels peaked early following administration of compound, then returned to control levels after 24 to 48 hours. Further, although expression of genes encoding glycolytic enzymes were similar between different organs, the kidney (FIG. 2A), liver (FIG. 2B), and lung (FIG. 2C) showed differences in both increases in relative expression levels and duration of the increase in particular mRNAs. These differences relate, in part, to the different degree to which glycolytic activity provides a critical source of energy for the respective tissue, especially during times of stress. These results indicated that compounds of the invention specifically induce glycolytic effects, and these effects can differ by tissue.

Figure 3:
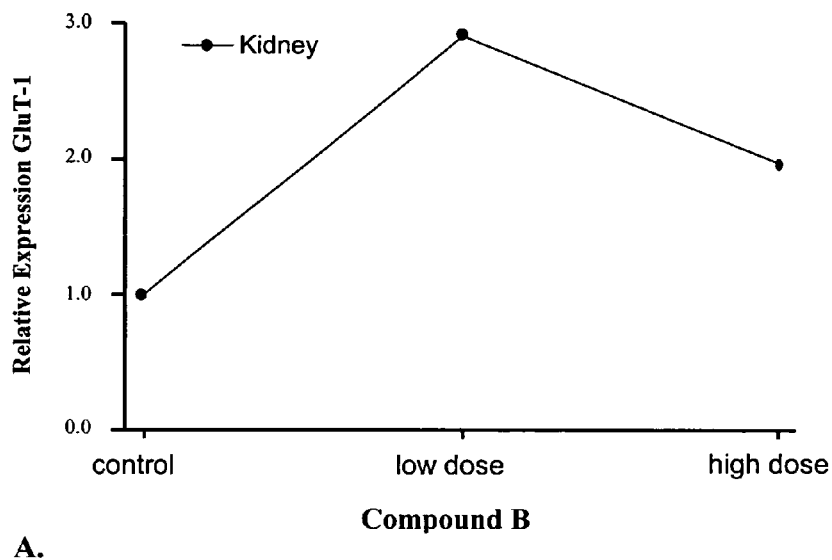
FIGS. 3A and 3B show dose and temporal response of genes encoding GluT-1 and IGFBP-1, respectively, in kidney and liver in animals treated with a compound of the invention.
Figure 3:
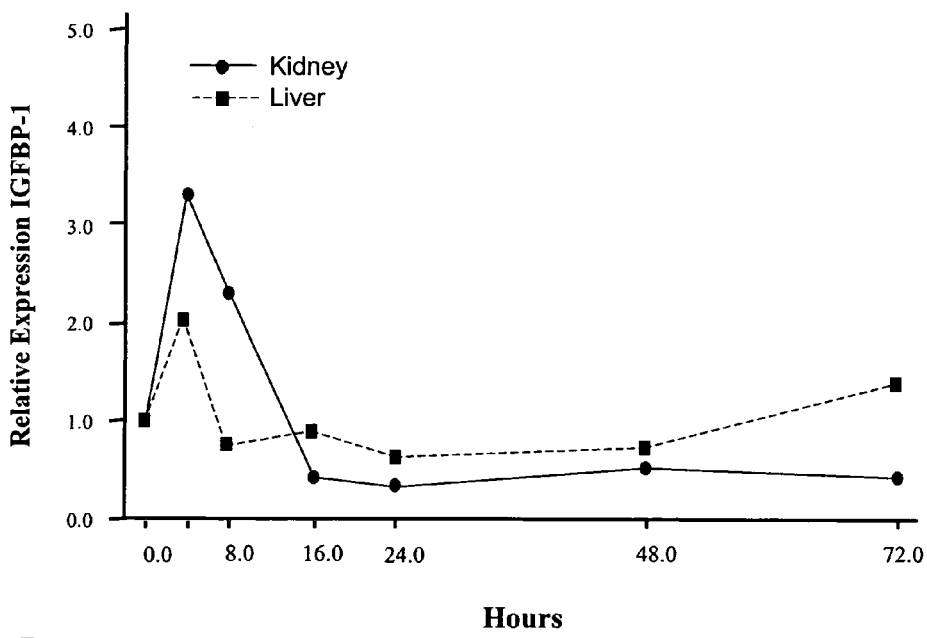

As shown in FIG. 3A, treatment with low dose (30 mg/ml) or high dose (100 mg/ml) of compound B resulted in a dose-dependent alteration in expression of the gene encoding GluT-1 in kidney. The increased expression of GluT-1 in this instance provides a mechanism by which blood glucose levels can be regulated by facilitating uptake of glucose by cells. As shown in FIG. 3B, treatment with compound B resulted in an almost identical temporal induction of IGFBP-1 expression in kidney and liver, but having a quantitatively different level of expression in one tissue compared to the other. IGFBP-1 facilitates transport of insulin-like growth factor, and increased circulating levels of IGFBP-1, as well as increased insulin sensitivity and glucose effectiveness, are associated with, for example, endurance training. (See, e.g., Manetta et al. (2003) Metabolism 52:821-826.) Therefore, compounds of the invention can specifically induce direct mediators of blood glucose uptake and indirect effects on hormonal regulators of blood glucose and glucose regulation.

Example 5

Increased Glucose Uptake

Insulin resistance is a decrease in the body's ability to respond to insulin. Insulin resistance, or decreased insulin sensitivity, is often associated with hyperglycemia, diabetes, and hyperinsulinaemia. A decrease in insulin resistance, or an increase in insulin sensitivity, is determined by measuring glucose uptake following administration of compounds of the present invention as follows.

To measure the effect of compounds of the present invention on glucose uptake in vivo, DIO (diet induced obese) rats (Charles River) are fed a high-fat diet for four weeks to induce obesity and insulin resistance. Alternately, ZDF rat, or any other genetic model of Type 2 diabetes, may be used. Animals are divided into treated and control groups. Treated animals receive compound for ten days while remaining on a high-fat diet. After ten days, fasted animals are instrumented with jugular, carotid, and femoral catheters under general anesthesia. A hyperinsulinemic-euglycemic clamp, a reference method for quantifying insulin resistance, is conducted with continuous infusion of insulin, and 10% glucose infused at a rate sufficient to maintain plasma glucose at basal concentrations. Blood samples are drawn to monitor blood glucose levels and to properly adjust the glucose infusion rate.

Under euglycemic steady-state conditions, the glucose infusion rate equals glucose uptake by all the tissues in the body and is therefore a measure of tissue insulin sensitivity. [3-$^3$H] glucose is infused before clamp procedure and during steady-state to estimate basal and insulin-stimulated whole body glucose turnover. Once steady-state glucose levels are achieved (~60-75 minutes), 2-deoxy-D-[1-$^{14}$C]glucose is administered as a bolus to estimate insulin-stimulated glucose uptake in individual tissues. Blood samples for measurements of glucose and tracer concentrations are taken at 1, 3, 5, 10, 20, 30 and 45 min after the bolus injection. Specific tissue uptake of glucose is determined from tissue samples harvested after euthanasia at 120 minutes. These methods are readily known to one skilled in the art.

Treating animals with compound of the present invention increases glucose uptake in tissues, such as muscle and liver, through enhanced sensitivity to insulin and reduced resistance to insulin. Enhanced glucose uptake following administration of compounds of the present invention indicates that compounds of the invention are useful to therapeutically reduce insulin resistance and increase insulin sensitivity in patients with insulin resistance, or with decreased or impaired insulin sensitivity. Methods and compounds of the present invention, therefore, increase glucose uptake in vivo and reduce blood glucose levels in patients with hyperglycemia, diabetes, or other deficiencies in regulating glucose homeostasis.

Example 6

Dose-dependent Decrease in Blood Glucose Levels

The effect of compound administration on blood glucose levels was examined as follows. Fifty male Sprague Dawley rats (6-7 weeks old) obtained from Simonsen, Inc. were dosed with 0.5% CMC (Sigma-Aldrich) or compound B at 20, 60, 100, or 200 mg/kg body weight by oral gavage once daily for 14 consecutive days. Animals were monitored for changes in body weight and signs of overt toxicity and mortality. On day 15, following an overnight fast with water available ad libitum, animals were anesthetized with isoflurane, the abdominal cavity was opened, and blood was collected from the inferior vena cava. One sample of approximately 1 ml was collected into tubes containing EDTA for hematological analysis, and a second sample of approximately 1 ml was collected into a tube with no anticoagulant for serum chemistry analysis. Blood sample analyses were performed by IDEXX (West Sacramento, Calif.).

Figure 4:
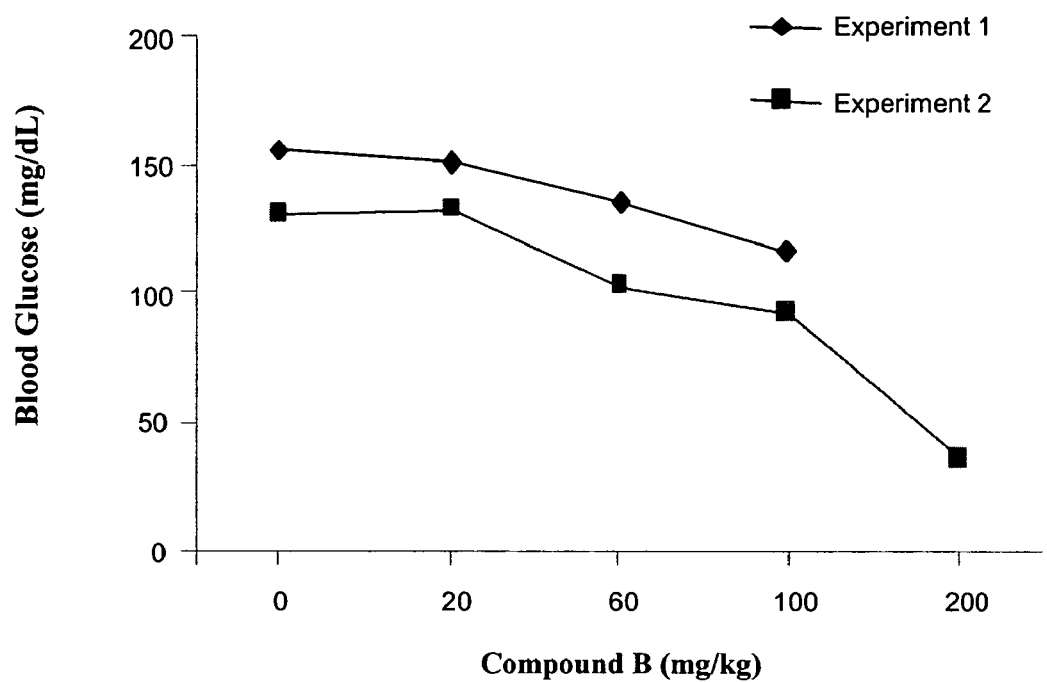
FIG. 4 shows reduction in blood glucose levels in animals treated with a compound of the invention.

As shown in FIG. 4, two separate experiments indicated that animals treated with compound of the invention showed a dose-dependent decrease in blood glucose levels. The relationship between compound dose and blood glucose levels suggested that blood glucose levels were maintained at desired levels with appropriate dosing using the methods and compounds of the present invention. Therefore, compounds and methods of the present invention are useful for regulating, and in particular, decreasing blood glucose levels. Further, the methods and compounds of the invention are useful to therapeutically decrease blood glucose levels in a subject, for example, wherein the subject has a disorder of glucose regulation such as, for example, hyperglycemia or diabetes.

Example 7

Increased Glucose Tolerance in an Animal Model of Diet-induced Type 2 Diabetes

C57Bl/6J mice fed a high-fat diet develop severe obesity, hyperglycemia, and hyperinsulinemia, and are a model of diet-induced obesity, Type 2 diabetes, and impaired glucose tolerance. Forty male C57BL/6J mice obtained from The Jackson Laboratory (Bar Harbor Me.) were divided into the following experimental groups: Group 1: vehicle control animals fed standard mouse chow (n=10); Group 2: animals fed standard mouse chow and administered 75 mg/kg/day compound E by oral gavage (n=10); Group 3: vehicle control animals fed high-fat mouse chow (45% fat from Research Diets) (n=10); Group 4: animals fed high-fat mouse chow and administered 75 mg/kg/day compound E by oral gavage (n=10). The feeding regimen was continued for 14 days with daily measurement of body weight and food consumption. Animals were then fasted for 4 hours prior to an Intra-Peritoneal Glucose Tolerance Test (IPGTT) using a glucose load of 2 g glucose/kg body weight. Blood samples were taken for determination of blood glucose levels at 0, 15, 30, 60, and 90 minutes following glucose administration.

Figure 5:
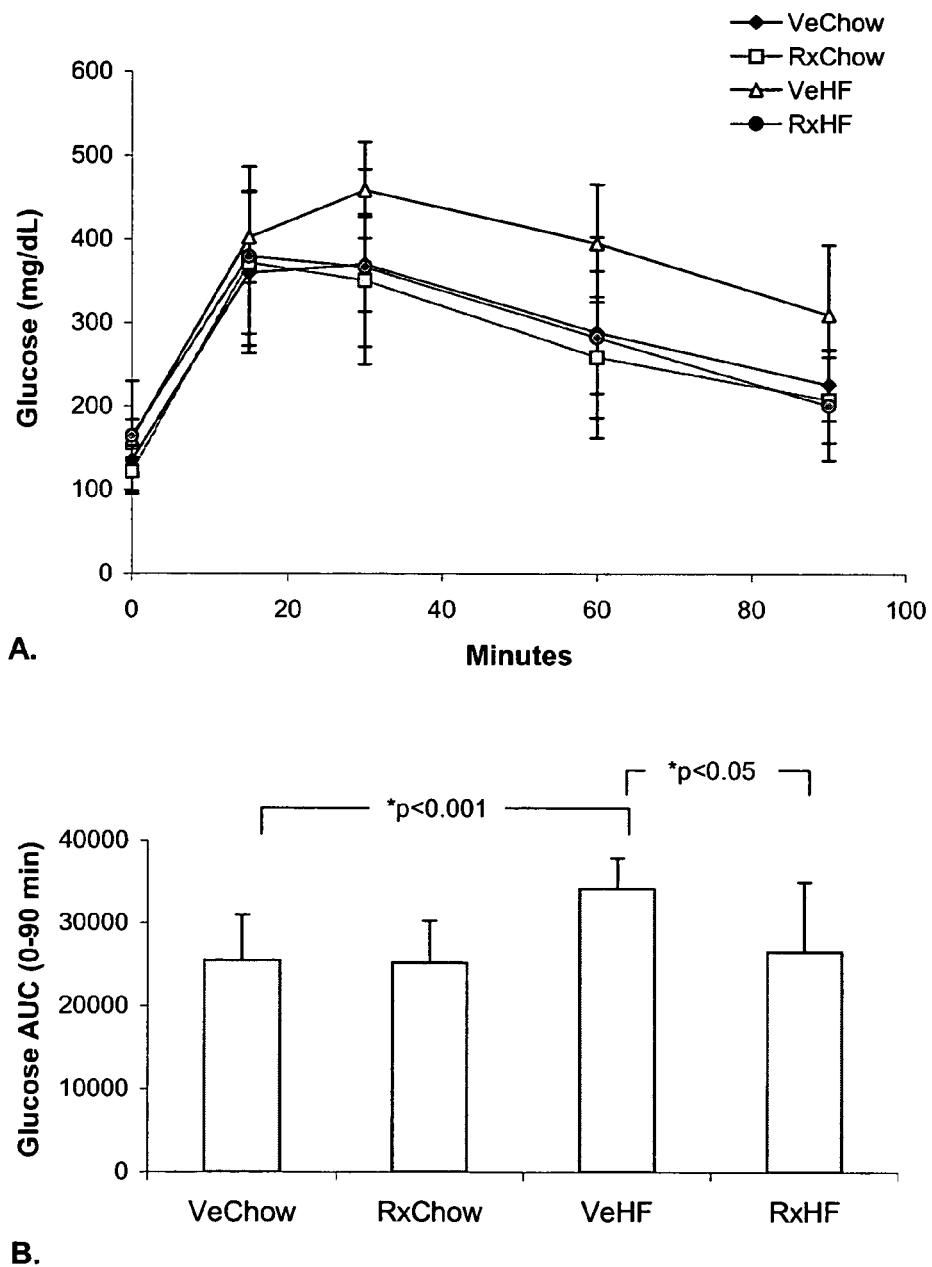
FIGS. 5A and 5B show increased glucose tolerance in an animal model of diet-induced Type 2 diabetes upon treatment with a compound of the invention.

As shown in FIG. 5A, mice on standard chow diet with (RxChow) or without (VeChow) compound administration cleared glucose at approximately the same rate and substantially the same as mice on high-fat diet treated with compound (RxHF). Mice on high-fat diet without compound (VeHF), however, cleared glucose at a lower rate than any of the other groups. Differences in calculated glucose area under the curve (AUC) for the IPGTT of individual animals comparing animals on standard chow treated with compound (RxChow) and without compound (VeChow) to animals on high-fat chow without compound (VeHF) were statistically significant (t-test, $p<0.001$). Additionally, a statistically significant difference in blood glucose levels was observed when comparing glucose AUC for animals on high-fat chow without compound (VeHF) to animals on high-fat chow treated with compound (RxHF) (t-test, $p<0.05$). (See FIG. 5B.) As indicated in FIG. 5B, however, there was no statistical difference in glucose AUC between treated mice on standard chow (RxChow) or high-fat diet (RxHF) and mice on standard chow without compound (VeChow).

These data indicated that treating animals with compound of the present invention improved glucose clearance from blood, decreased blood glucose levels, normalized glucose tolerance, and restored glucose homeostasis in an animal model of diet-induced obesity and impaired glucose tolerance. These results were suggestive of improved glucose utilization and regulation in treated animals. This restoration of normal glucose tolerance by compounds of the present invention in a model of diet-induced impairment of glucose utilization and regulation (e.g., impaired glucose tolerance) indicates that methods and compounds of the present invention are useful to therapeutically restore glucose homeostasis in patients with impaired glucose tolerance.

Improved glucose utilization and regulation and restored glucose homeostasis following administration of compounds of the present invention can also be determined using an Oral Glucose Tolerance Test (OGTT). A similar experiment to that described above in Example 7 is performed to measure the effect of compound administration on blood glucose levels. Forty male C57BL/6J mice are divided into the following experimental groups: Group 1: vehicle control animals are fed standard mouse chow (n=10); Group 2: vehicle control animals are fed high-fat mouse chow (45% fat from Research Diets) (n=10); Group 3: animals are fed high-fat mouse chow and administered 75 mg/kg/day compound E by oral gavage (n=10); Group 4: animals are fed high-fat mouse chow and administered 75 mg/kg/day compound A by oral gavage (n=10). The feeding regimen is continued for 28 days with weekly measurement of body weight. Animals are then fasted overnight prior to an OGTT using a glucose load of 1 g glucose/kg body weight. Blood samples are taken for glucose levels at 0, 30, 60, 90, 120, and 180 minutes following glucose administration.

Example 8

Decreased Glycation of Hemoglobin

Glycated hemoglobin is formed by the attachment of various sugars (most commonly glucose) to the hemoglobin molecule, and is formed at a rate that is directly proportional to the blood glucose concentration. Measurement of glycated hemoglobin levels gives an accurate index of the mean blood glucose concentration over the preceding 2 to 3 months. Clinically, glycated hemoglobin levels provide an assessment of glycemic control in diabetic patients or in patients with hyperglycemia.

The effect of compound administration on glycated hemoglobin levels was examined using a mouse model of diabetes as follows. Twenty male db/db mice (Harlan) received drinking water containing either vehicle (100 µM histidine) or compound A (0.5 mg/ml) for a period of 8 weeks. Prior to study initiation and at weeks 4 and 8 following treatment, blood samples were collected from the tail vein and HbA1c levels were measured using an HbA1cNOW kit (Metrika Inc., Sunnyvale Calif.).

Figure 6:
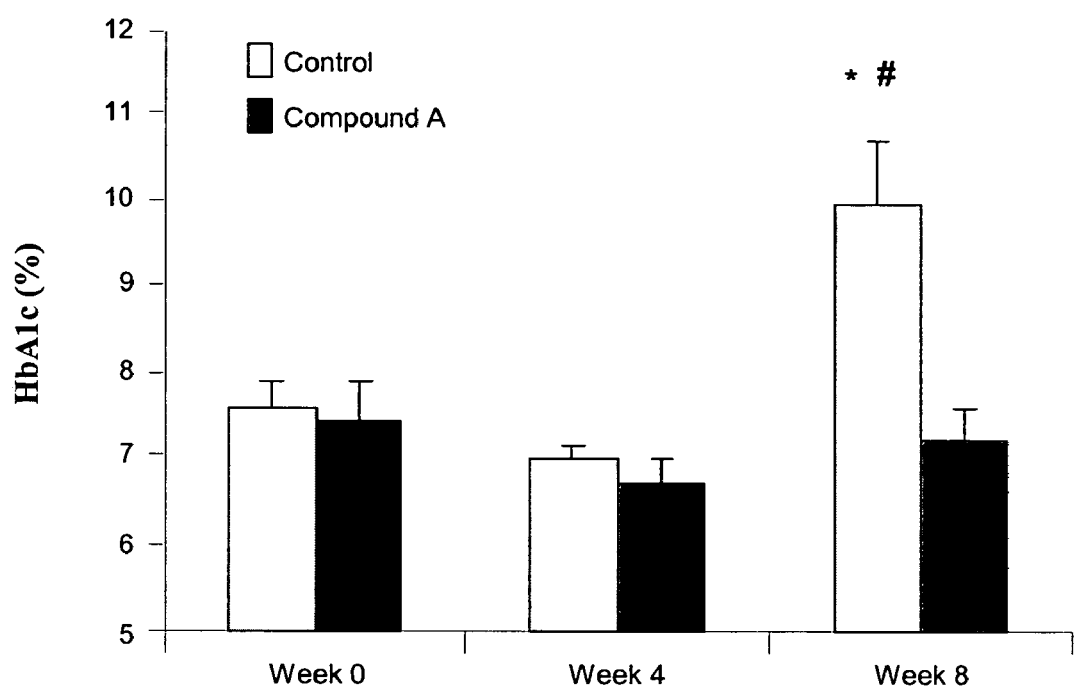
FIG. 6 shows decreased glycation of hemoglobin in db/db mice treated with a compound of the invention.

HbA1c levels were significantly increased ($p<0.05$) from baseline at 8 weeks in the control group (FIG. 6). As shown in FIG. 6, HbA1c increased from about 7.5% at week 0 to about 10% at week 8. The HbA1c levels in the compound-treated group did not increase over time and were significantly lower than the non-treated values at week 8. HbA1c levels in animals treated with compound of the present invention were about 7.5% at week 8.

These data showed that treatment of animals with compound of the present invention reduced the accumulation of glycated hemoglobin in a model of Type 2 diabetes. HbA1c is a reflection of overall glycemic control in diabetic patients. This reduction of HbA1c in this model by compound of indicates that such compounds of the invention are useful to therapeutically improve glycemic control in patients with diabetes or hyperglycemia.

Example 9

Reduced Body Weight Gain and Reduced Fat Stores

The effect of compounds of the present invention on weight loss and fat stores in animals was examined as follows. Fifty male Sprague Dawley rats (6-7 weeks old) obtained from Simonsen, Inc. were dosed with 0.5% CMC (Sigma-Aldrich) or compound B at 20, 60, 100, or 200 mg/kg body weight by oral gavage once daily for 14 consecutive days. Animals were monitored for changes in body weight and signs of overt toxicity and mortality. On day 15, following an overnight fast with water available ad libitum, animals were anesthetized with isoflurane. One whole blood sample of approximately 1 ml was collected into tubes containing EDTA for hematological analysis, and a second sample of approximately 1 ml was collected into a tube with no anticoagulant for serum chemistry analysis. Blood sample analyses were performed by IDEXX (West Sacramento, Calif.). Following blood collection, the diaphragm was incised and the animals were sacrificed. Macroscopic observations were recorded for each animal and the liver, kidneys, heart, spleen, lungs, stomach, small intestines, and large intestines were collected for histological assessment.

Figure 7:
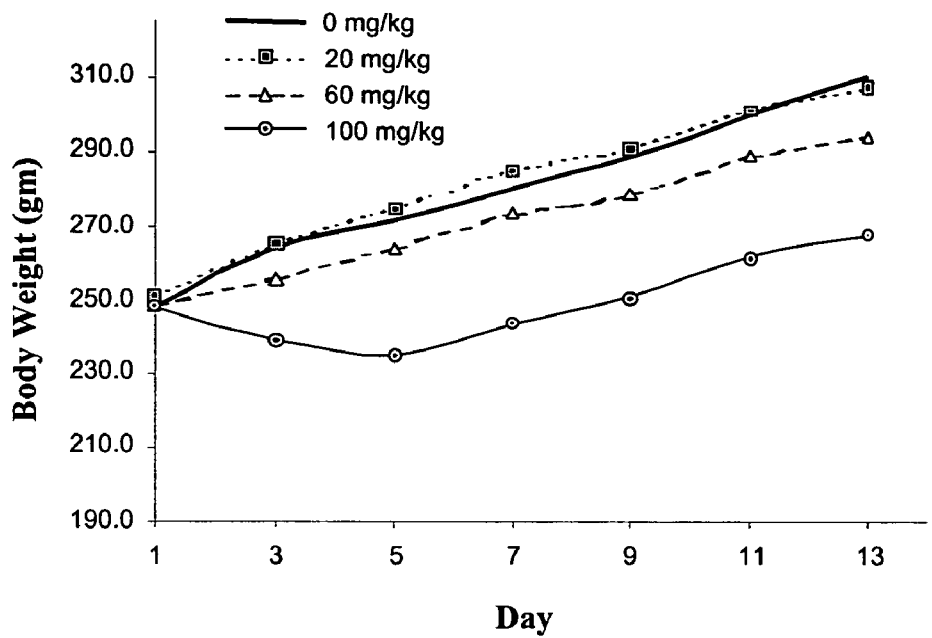
FIGS. 7A and 7B show changes in body weight and heart weight in animals treated with a compound of the invention.
Figure 7:
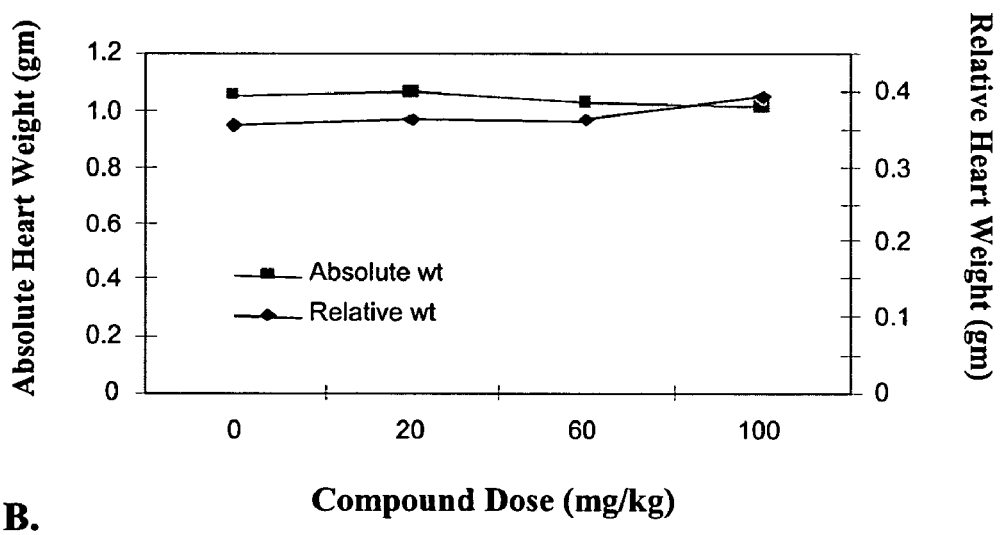

As shown in FIG. 7A, animals treated with compounds of the invention showed a dose-dependent retardation in weight gain. Examination of animals indicated that there was not a general retardation in growth, as the absolute weight of most organs in treated animals was not significantly different than the respective organ weights in control, untreated animals. For example, the absolute heart weight in animals treated with compound compared to control showed no statistically significant difference (FIG. 7B). However, the relative organ weight was significantly increased in treated animals relative to untreated controls. For example, the relative heart weight, expressed as a fraction of the total body weight, compared to control, was significantly increased in animals treated with compound at 100 mg/kg ($p=0.036$, one-way ANOVA/Tukey's test).

Figure 8:
FIG. 8 shows reduction in visceral fat in animals treated with a compound of the invention.
Figure 8:

Since absolute organ weight, e.g., heart weight, was not significantly decreased, there is not a general growth retardation process in treated animals. Further, since organ weight relative to total body weight was significantly increased, there was selective loss of another tissue. As shown in FIG. 8, the animals showed a dose-dependent reduction in visceral fat when treated with compound. The arrow in the top panel shows visceral fat pads present in animals treated with low doses of compound, whereas the panel on the bottom shows a complete absence of fat pads in animals treated with higher doses of compound.

These results indicated that compounds and methods of the present invention are useful for regulating body weight, inducing loss or reduction in body mass, without concomitant loss of muscle mass, and decreasing visceral fat. Taken together, these results indicated that methods and compounds of the present invention affectively controlled weight gain and, in particular, reduced visceral fat. Such methods and compounds are advantageous in treatment or prevention of obesity, and are thus useful for treating or preventing diabetes associated with obesity.

Example 10

Reduced Body Weight Gain in an Animal Model of Diet-induced Obesity

C57B1/6J mice fed a high-fat diet develop severe obesity, hyperglycemia, and hyperinsulinemia, and are a model of diet-induced obesity, Type 2 diabetes, and impaired glucose tolerance. Forty male C57BL/6J mice obtained from The Jackson Laboratory (Bar Harbor Me.) were divided into the following experimental groups: Group 1: vehicle control animals fed standard mouse chow (n=10); Group 2: vehicle control animals fed high-fat mouse chow (45% fat from Research Diets) (n=10); Group 3: animals fed high-fat mouse chow and administered 75 mg/kg/day compound E by oral gavage (n=10); Group 4: animals fed high-fat mouse chow and administered 75 mg/kg/day compound A by oral gavage (n=10). The feeding regimen was continued for 28 days with weekly measurement of body weight. Animals were then sacrificed and their organs and fat pads were harvested and weighed.

Figure 9:
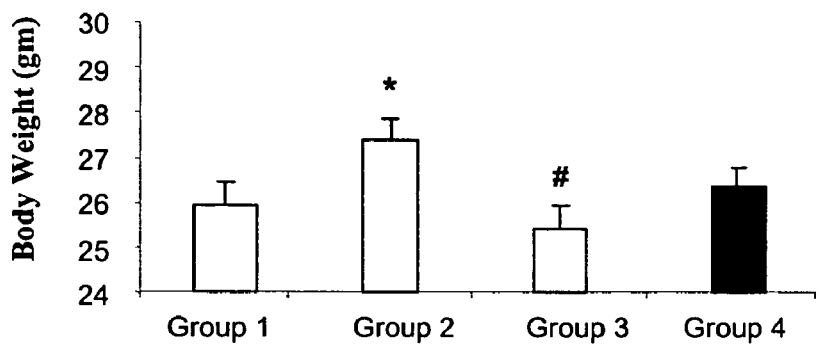
FIGS. 9A, 9B, and 9C show decreased body weight gain and abdominal fat pad weight in an animal model of diet-induced obesity upon treatment with a compound of the invention.
Figure 9:
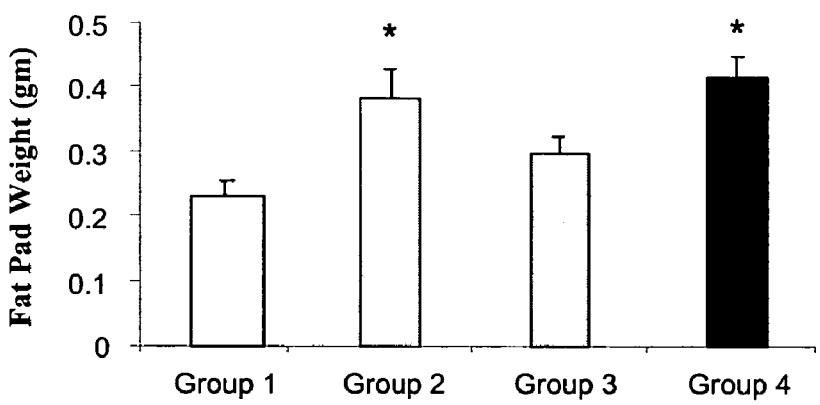
Figure 9:
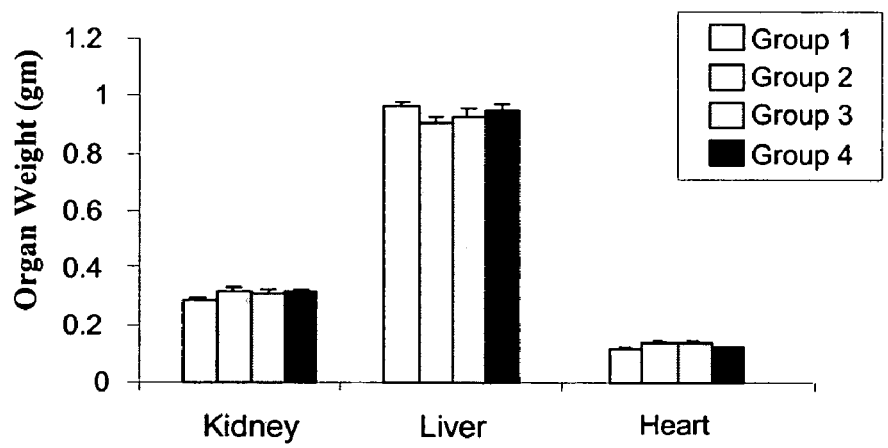

As shown in FIG. 9A, animals fed a high-fat diet (group 2) had a significantly higher body weight than animals fed standard chow (group 1) ($p<0.05$). However, animals fed high-fat diet but treated with compound E or compound A (group 3 and group 4, respectively) showed significantly less weight gain ($p<0.05$). In fact, despite the high-fat diet, animals treated with compound had essentially the same weight as animals fed a normal diet (compare group 3 and group 4 with group 1). Similarly, as shown in FIG. 9B, animals fed a high-fat diet (group 2) had a significant increase in abdominal fat pad weight compared to both animals fed standard chow (group 1) and animals fed high-fat diet that were also treated with compound of the invention (group 3 and group 4). As can be seen in FIG. 9B, animals fed the high-fat diet and treated with compound had essentially the same fat pad weight as animals fed a normal diet.

The weights of various organs of the animals were also measured following the 28-day study. As shown in FIG. 9C, organ weights of kidney, liver, and heart were not different between any of experimental groups. These results indicated that the observed differences in body weight were attributed to decreases in fat stores and not decreased growth rate. These data showed that treatment of animals with compounds of the invention eliminated the increase in body weight associated with having a high-fat diet. This prevention of weight gain by compounds of the invention indicated that compounds of the invention are useful to therapeutically reduce weight gain even under adverse dietary intake. Further, modulation of weight gain by the methods and compounds of the present invention suggest that such compounds are potentially useful to therapeutically modulate weight loss in obese patients.

Example 11

Weight Loss in Obese Mouse

The effect of administration of compounds of the present invention on weight loss in animals is examined as follows. C57BL/6J mice are obtained from The Jackson Laboratory (Bar Harbor Me.). C57B1/6J mice fed a high-fat diet develop severe obesity, hyperglycemia, and hyperinsulinemia, and are a model of diet-induced obesity, Type 2 diabetes, and impaired glucose tolerance. Mice are fed high-fat chow (45% of calories from fat) for 8 weeks, after which the mice are obese. Obese mice are divided into two experimental groups: Group 1 animals are control obese mice and Group 2 animals are obese mice treated with compound of the present invention. An additional group of age matched non-obese mice are also included in the study. Animals are then treated daily with compound of the invention or with vehicle control. Body weight of the mice is measured twice a week for 21 days. On day 21 the animals are weighed and then sacrificed. Abdominal fat pads, liver, kidney, and heart are isolated and weighed for analysis.

Loss of body weight upon administration of compound indicates that compounds of the invention are useful to therapeutically reduce body weight in obese patients.

Example 12

Increased Expression of Genes Involved in Regulation of Blood Pressure

Hypertension is a risk factor for diabetes and disorders and diseases associated with diabetes. The effects of compounds of the present invention on regulation of blood pressure were examined as follows. Animals were treated with compound B or compound D and RNA samples were prepared as described above in Example 4. For measurement of iNOS mRNA levels, the following methods were used. cDNA synthesis was performed using 1 µM random hexamer primers, 1 µg of total RNA, and OMNISCRIPT reverse transcriptase (Qiagen), according to the manufacturer's instructions. Resulting cDNA was diluted 5-fold with water to give 100 µL final volume. Analysis of the relative level of gene expression was performed by quantitative PCR using a FASTSTART DNA MASTER SYBR GREEN I kit (Roche) and gene-specific primers, using a LIGHTCYCLER system (Roche), according to manufacturer's instructions. Samples were heated to 94° C. for 6 minutes and then cycled through 95° C. for 15 seconds, 60° C. for 5 seconds, and 72° C. for 10 seconds for a total of 42 cycles. Inducible nitric oxide synthase (iNOS)-specific primers were as follows:

```
m-iNOS-F2    CCCAGGAGGAGAGAGATCCGATT    (SEQ ID NO: 1)
m-iNOS-R2    AGGTCCCTGGCTAGTGCTTCAGA    (SEQ ID NO: 2)
```

The relative level of 18S ribosomal RNA gene expression was measured as a control. Quantitative PCR was performed using a QUANTITECT SYBR GREEN PCR kit (Qiagen) and gene-specific primers, using a LIGHTCYCLER system (Roche), according to manufacturer's instructions. Samples were heated to 95° C. for 15 minutes and then cycled through 94° C. for 15 seconds, 60° C. for 20 seconds, 72° C. for 10 seconds for a total of 42 cycles. Ribosomal RNA-specific primers were as follows:

```
18S-rat-2B   TAGGCACGGCGACTACCATCGA    (SEQ ID NO: 3)
18S-rat-2A   CGGCGGCTTTGGTGACTCTAGAT   (SEQ ID NO: 4)
```

Each PCR run included a standard curve and water blank. In addition, a melt curve was run after completion of each PCR run to assess the specificity of the amplification. iNOS gene expression was normalized relative to the expression level of 18S ribosomal RNA for that sample.

Figure 10:
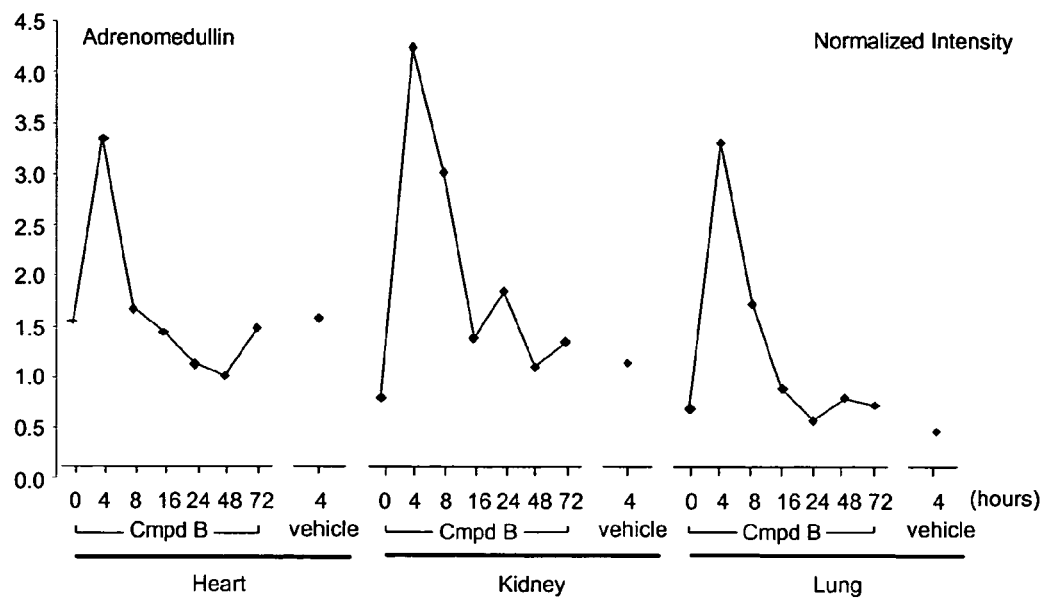
FIGS. 10A and 10B show expression of the gene encoding inducible nitric oxide synthase (iNOS) and adrenomedullin following treatment with compounds of the present invention.
Figure 10:
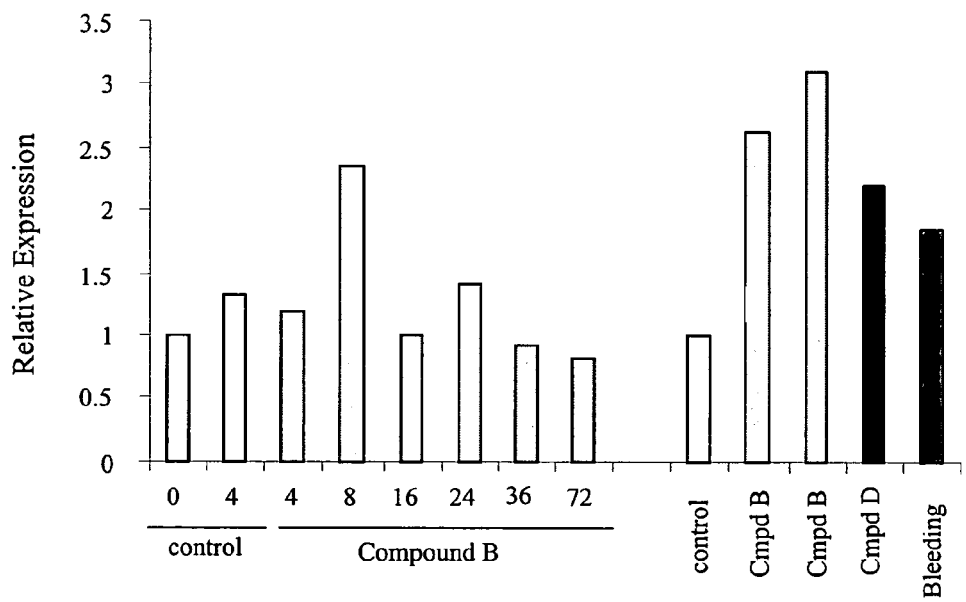

As shown in FIG. 10A, expression of the gene encoding iNOS increased within 8 hours following treatment with compounds of the present invention, and then returned to control levels thereafter. Further, the induction of iNOS was dose-dependent and was achieved with two different compounds of the present invention (compound B and compound D). These two compounds are exemplary of two different pharmacophores, a phenanthroline derivative and a heterocyclic carboxamide, that can be used in the present methods. These results indicated that treatment with compounds of the present invention increased iNOS expression, a protein involved in vasodilatory regulation. Therefore, compounds and methods of the present invention are useful for inducing vasodilation and reducing blood pressure.

For measurement of adrenomedullin mRNA expression, samples were prepared and were hybridized and analyzed as described above in Example 4. As shown in FIG. 10B, expression of adrenomedullin, a representative gene encoding a protein involved in vasodilation, was increased in various tissues in animals treated with compound B of the present invention. In the time course following treatment with compound B, adrenomedullin mRNA levels in heart, kidney, and lung showed a rapid increase in expression and then returned to control levels within 16 to 24 hours.

Taken together, these results showed that methods and compounds of the present invention provide means for activating expression of genes involved in regulating blood pressure through vasodilatory mechanisms. Such genes include, but are not limited to, inducible nitric oxide synthase and adrenomedullin. Therapeutic upregulation of vasodilatory factors provides an effective means for reducing blood pressure and, thereby, providing benefit in patients with metabolic disorders, e.g., diabetes. By reducing blood pressure, methods and compounds of the present invention provide a means for treating or preventing diabetes and other metabolic disorders associated with diabetes, hyperglycemia, etc.

Example 13

Reduction of Serum Triglycerides

The effect of compound administration on triglyceride levels was examined using a mouse model of diabetes as follows: Twenty male db/db mice (Harlan, Indianapolis, Ind.), which carry a homozygous loss-of-function mutation in the leptin receptor, were used for this study. Triglyceride levels are typically elevated 1.5-2 times in db/db mice compared to that in normal mice. (Nishina et al (1994) Metabolism 43:549-553.) Triglyceride levels in db/db mice progressively increase with age. (Tuman and Doisy (1977) Diabetologia 13:7-11.) Mice received drinking water containing either vehicle (100 µM histidine) or compound A (0.5 mg/ml in 100 µM histidine) for a period of 8 weeks. At the termination of the study, animals were fasted overnight and blood samples were taken from the caudal vena cava under general anesthesia and placed in serum separator tubes. Blood samples were sent to Quality Clinical Labs (Mountain View, Calif.) for analysis.

Figure 11:
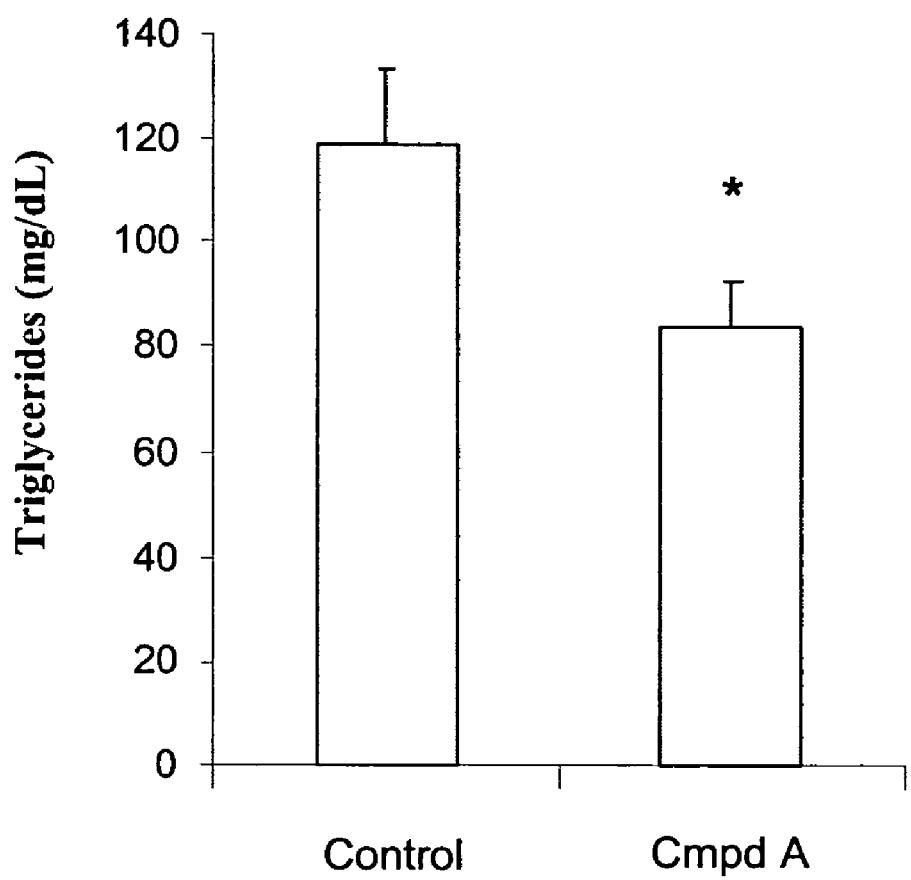
FIG. 11 shows triglyceride levels in animals treated with a compound of the present invention.

As shown in FIG. 11, triglyceride levels were approximately 120 mg/dL in control db/db mice at the end of the experiment. However, the triglyceride level in animals treated with compound of the invention was approximately 85 mg/dL, significantly lower than controls. Increased triglyceride levels are associated with increased risk of cardiovascular disease, and elevated triglycerides are a component of the, metabolic syndrome. As the compounds and methods of the invention effectively lower or maintain triglyceride levels in conditions normally associated with elevated triglycerides, e.g., diabetes, syndrome X, macrovascular disease, or other dyslipidemias, the present methods are useful for treating individuals having or at risk of having such conditions.

Example 14

Identification of Compounds and HIFα Stabilization

Compounds that modulate HIF-specific prolyl hydroxylase activity can be identified using an assay based on the hydroxylation-coupled decarboxylation of 2-oxo[1-$^{14}$C]glutarate. (See Hirsila et al (2003) J. Biol. Chem. 278:30772-30780.) The reaction is performed in a 1.0 ml reaction volume containing 10-100 μL of detergent, e.g., Triton-X-100, solubilized cell extract obtained from cells expressing either endogenous HIF prolyl hydroxylase or a recombinant HIF prolyl hydroxylase; 0.05 μmol substrate peptide, e.g., DLDLEMLAPYIPMDDDFQL (SEQ ID NO: 5); 0.005 μmol of FeSO$_4$, 0.16 μmol of 2-oxo[1-$^{14}$C]glutarate, 2 μmol of ascorbate, catalase, 0.1 μmol dithiothreitol, and 50 μmol Tris-HCl buffer, adjusted to pH 7.8 at 25° C. The enzyme reaction is carried out at 37° C. for 20 minutes. The $^{14}$CO$_2$ produced by the reaction is captured on base-impregnated filter paper suspended in the atmosphere over the reaction mixture and counted in a scintillation counter.

Stabilization of HIFα using compounds and methods of the present invention was examined as follows. Human cells derived from adenovirus-transformed fetal kidney epithelium (293A), cervical epithelial adenocarcinoma (HeLa), hepatocellular carcinoma (Hep3B), squamous carcinoma (SSC-25), and lung fibroblast (HLF) (see, e.g., American Type Culture Collection, Manassas Va.; and Qbiogene, Carlsbad Calif.) were separately seeded into 100 mm culture dishes and grown at 37° C., 20% O$_2$, 10% CO$_2$ in media as follows: HeLa cells in Dulbecco's Modification of Eagle's Medium (DMEM), 2% fetal bovine serum (FBS); HLF cells in DMEM, 10%FBS; 293A cells in DMEM, 5%FBS; and Hep3B cells in Minimal Essential Medium (MEM), Earle's BSS (Mediatech Inc., Herndon Va.), 2 mM L-glutamine, 0.1 mM non-essential amino acids, 1 mM sodium pyruvate, 10% FBS. When cell layers reached confluence, the media was replaced with OPTI-MEM media (Invitrogen Life Technologies, Carlsbad Calif.) and cell layers were incubated for approximately 24 hours in 20% O$_2$, 10% CO$_2$ at 37° C. Compound of the invention (one of compounds B, F, G, and H) or DMSO (0.5 to 1%) was then added to existing medium, and incubation was continued overnight.

Following incubation, the media was removed, centrifuged, and stored for analysis. The cells were washed two times in cold phosphate buffered saline (PBS) and then lysed in 1 ml of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates were centrifuged at 3,000×g for 5 minutes at 4° C., and the cytosolic fractions (supernatant) were collected. The nuclei (pellet) were resuspended and lysed in 100 μl of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) were collected.

Figure 12:
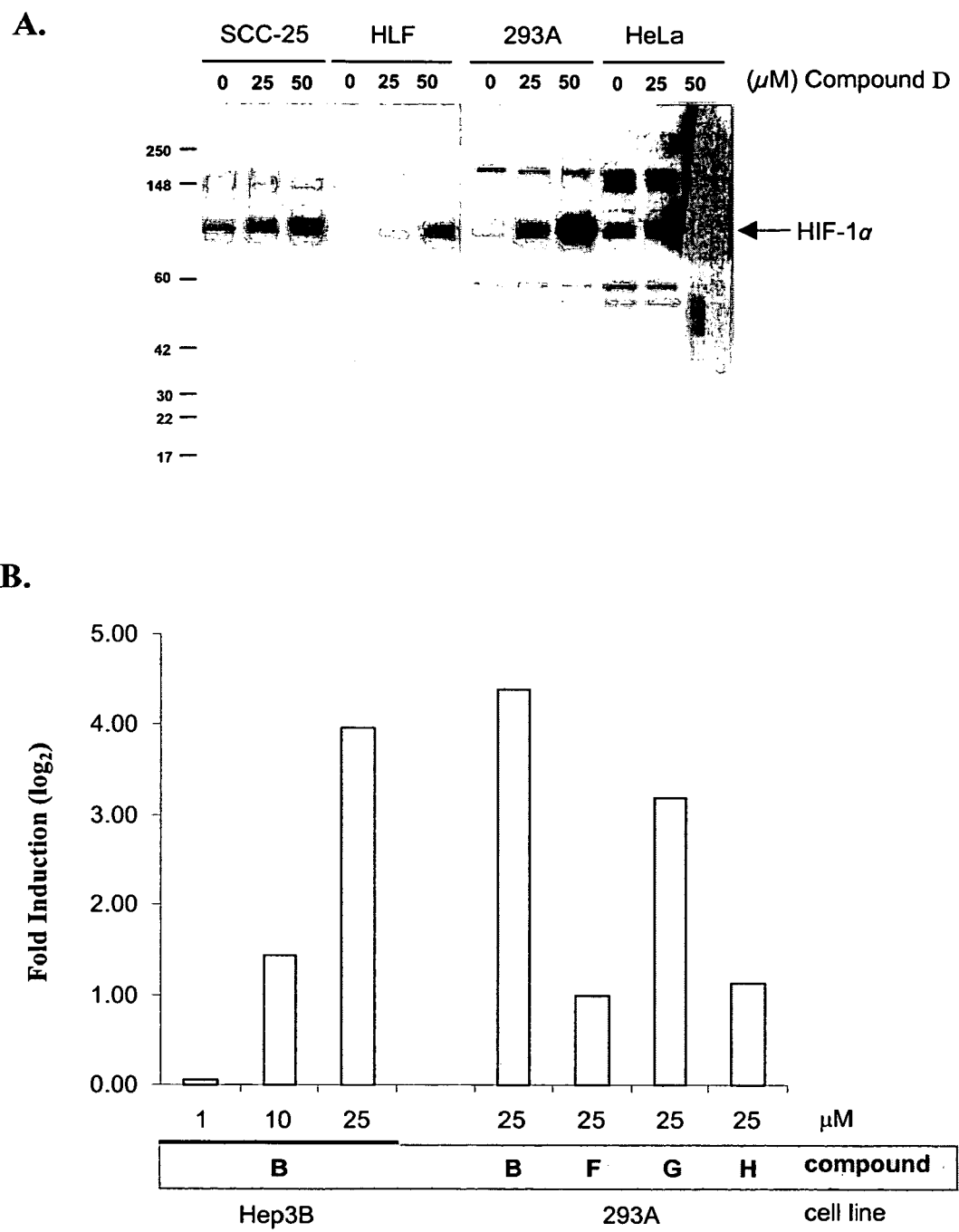
FIGS. 12A and 12B show HIF-1α stabilization in cells treated with compounds of the invention.

Nuclear fractions were normalized based on protein concentration and loaded onto a 4-12% TG gel and fractionated under reducing conditions. Proteins were transferred to a PVDF membrane (Invitrogen Corp., Carlsbad Calif.) at 500 mA for 1.5 hours. The membrane was blocked in T-TBS, 2% milk for 1 hour at room temperature and incubated overnight with mouse anti-human HIF-1α antibody (BD Biosciences, Bedford Me.), diluted 1:250 in T-TBS, 2% milk. The blot was developed using SUPERSIGNAL WEST chemiluminescent substrate (Pierce, Rockford Ill.). As shown in FIGS. 12A, a representative compound of the invention (compound D) stabilized HIFα in a dose-dependent manner in various cell types, allowing HIFα to accumulate within the cells.

Alternatively, nuclear fractions were prepared using a Nuclear Extract kit (Active Motif, Carlsbad Calif.) and were analyzed for HIF-1α using a TRANSAM HIF-1 ELISA kit (Active Motif) according to the manufacturer's instructions. As seen in FIG. 12B, Hep3B cells showed dose-dependent stabilization of HIFα when treated with a compound of the invention. FIG. 12B also shows epithelial cells (293A) and hepatocellular carcinoma (Hep3B) treated with various compounds of the invention (Compounds B, F, G, and H) showed stabilization and accumulation of HIFα compared to vehicle-treated control cells.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

---

What is claimed is:

1. A method for treating diabetes in a diabetic subject, the method comprising administering to the subject an effective amount of a heterocyclic carbonyl glycine compound which inhibits a hypoxia inducible factor (HIF) hydroxylase, thereby treating diabetes in the subject.

2. A method for treating hyperglycemia in a hyperglycemic subject, the method comprising administering to the subject an effective amount of a heterocyclic carbonyl glycine compound which inhibits a HIF hydroxylase, thereby treating hyperglycemia in the subject.

3. A method for decreasing blood glucose levels in a diabetic or hyperglycemic subject, the method comprising administering to the subject an effective amount of a heterocyclic carbonyl glycine compound which inhibits a HIF hydroxylase, thereby decreasing blood glucose levels in the subject.

4. The method of any one of claims 1, 2, and 3, wherein the HIF hydroxylase is a HIF prolyl hydroxylase.

5. The method of any one of claims 1, 2, and 3, wherein the subject is a mammal.

6. The method of claim 5, wherein the mammal is a human.

7. The method of any one of claims 1, 2, and 3, wherein the compound is [(7-Chloro-3-hydroxy-quinoline-2-carbonyl)-amino]-acetic acid.

8. The method of any one of claims 1, 2, and 3, wherein the compound is [(1-Chloro-4-hydroxy-isoquinoline-3-carbonyl)-amino]-acetic acid.

9. The method of any one of claims 1, 2, and 3, wherein the compound is [(4-Hydroxy-7-phenoxy-isoquinoline-3-carbonyl)-amino]-acetic acid.

10. The method of any one of claims 1, 2, and 3, wherein the compound is [(1-Chloro-4-hydroxy-7-methoxy-isoquinoline-3-carbonyl)-amino]-acetic acid.

11. The method of any one of claims 1, 2, and 3, wherein the compound is [(3-Hydroxy-6-isopropoxy-quinoline-2-carbonyl)-amino]-acetic acid.

12. The method of any one of claims 1, 2, and 3, wherein the compound is [(3-Hydroxy-pyridine-2-carbonyl)-amino]-acetic acid.

13. The method of any one of claims 1, 2, and 3, wherein the compound is [(7-Benzyloxy-1-chloro-4-hydroxy-isoquinoline-3-carbonyl)-amino]-acetic acid methyl ester.

14. The method of claim 4, wherein the HIF prolyl hydroxylase is selected from the group consisting of EGLN1, EGLN2, and EGLN3.

15. The method of any one of claims 1, 2, and 3, wherein the heterocyclic carbonyl glycine is a substituted quinoline-2-carboxamide or esters thereof; a substituted isoquinoline-3-carboxamide or esters thereof; a 3-methoxy pyridine carbonyl glycine or esters thereof; a 3-hydroxypyridine carbonyl glycine or esters thereof; or a 5-sulfonamideocarbonyl pyridine carboxylate or esters thereof.

* * * * *